US012704500B2

(12) United States Patent
Bucher et al.

(10) Patent No.: US 12,704,500 B2
(45) Date of Patent: Aug. 11, 2026

(54) PARALLELIZED PROBING OF A PLURALITY OF SAMPLES IN A SELF-ORGANIZED STRUCTURE

(71) Applicant: TECHNISCHE UNIVERSITÄT MÜNCHEN, Munich (DE)

(72) Inventors: Dominik Bucher, Puchheim (DE); Robin Derek Allert, Eching (DE); Andreas Deeg, Munich (DE)

(73) Assignee: Technische Universität München, Munich (DE)

( * ) Notice: Subject to any disclaimer, the term of this patent is extended or adjusted under 35 U.S.C. 154(b) by 118 days.

(21) Appl. No.: 18/290,283

(22) PCT Filed: May 17, 2022

(86) PCT No.: PCT/EP2022/063262
§ 371 (c)(1),
(2) Date: Nov. 10, 2023

(87) PCT Pub. No.: WO2022/243281
PCT Pub. Date: Nov. 24, 2022

(65) Prior Publication Data
US 2024/0241105 A1 Jul. 18, 2024

(30) Foreign Application Priority Data
May 18, 2021 (EP) .................................... 21174441

(51) Int. Cl.
*G01N 33/487* (2006.01)
*G01N 33/543* (2006.01)

(52) U.S. Cl.
CPC ... *G01N 33/48707* (2013.01); *G01N 33/5438* (2013.01)

(58) Field of Classification Search
CPC ........ B01L 2200/0668; G01N 15/1436; G01N 15/1459; G01N 15/1484; G01N 21/253; G01N 21/6453
See application file for complete search history.

(56) References Cited

U.S. PATENT DOCUMENTS

| | | | |
|---|---|---|---|
| 9,658,301 | B2 | 5/2017 | Walsworth |
| 2012/0184464 | A1 | 7/2012 | Lee et al. |

(Continued)

FOREIGN PATENT DOCUMENTS

| | | | |
|---|---|---|---|
| EP | 3656472 | A1 | 5/2020 |
| WO | 2018052497 | A2 | 3/2018 |

OTHER PUBLICATIONS

International Search Report and Written Opinion in Application No. PCT/EP2022/063262 dated Sep. 12, 2022, 15 pages.

(Continued)

*Primary Examiner* — Thanh Luu
(74) *Attorney, Agent, or Firm* — Barclay Damon LLP

(57) ABSTRACT

Disclosed herein is a method for parallelized probing of a plurality of samples, a sensor chip for parallelized probing of a plurality of samples, a sensing device for parallelized probing of a plurality of samples, and a measurement system for parallelized probing of a plurality of samples. The method comprises providing a sensor chip, the sensor chip comprising a sensing layer arranged in or on a substrate and a measurement volume adjacent to the sensing layer. The sensing layer comprises a plurality of sensing elements, each of which is configured to generate a sensor signal characterizing a physical observable in the vicinity of the respective sensing element. A carrier fluid comprising a plurality of sample objects is provided to the measurement volume, wherein each of the sample objects comprises or forms a respective sample. A number of sample objects in the measurement volume is controlled such that the sample (Continued)

Figure 1A:
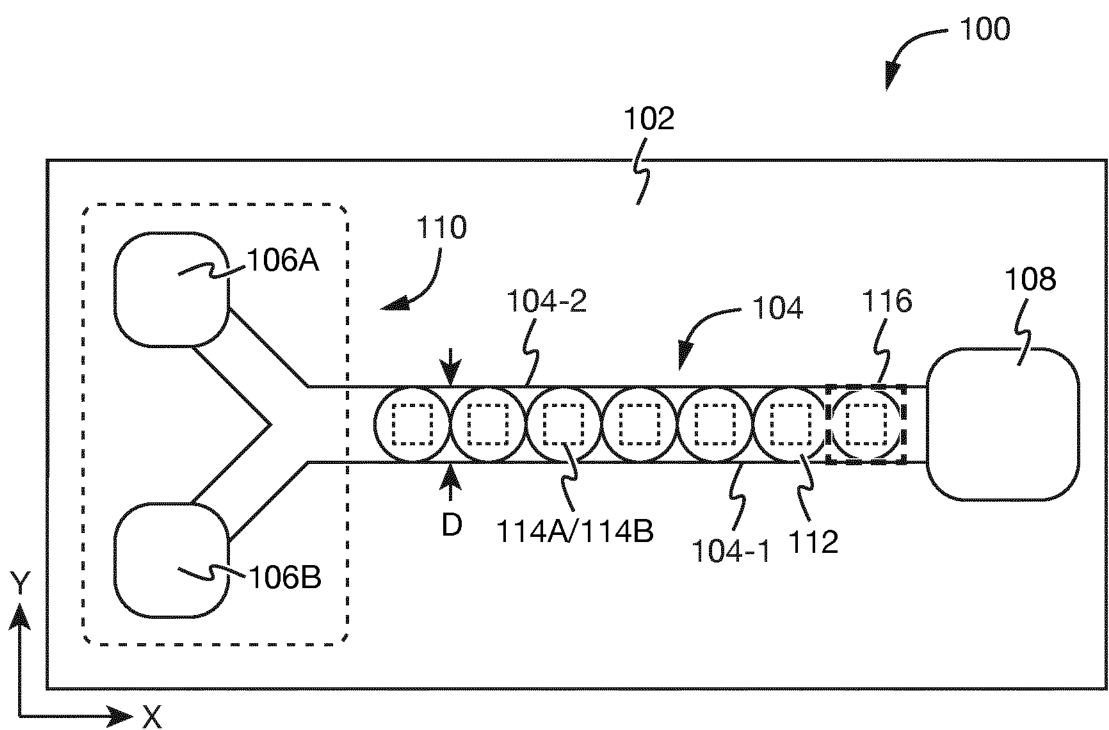

objects form a self-organized structure in the measurement volume. The self-organized structure is a structure in which the arrangement of the sample objects is at least in part defined by interactions between the sample objects themselves. A measurement is performed on one or more of the samples while the sample objects are arranged in the self-organized structure, wherein a measurement on a sample is performed using one or more sensing elements arranged adjacent to the respective sample object in the self-organized structure.

20 Claims, 9 Drawing Sheets

(56) References Cited

U.S. PATENT DOCUMENTS

| | | | | |
|---|---|---|---|---|
| 2016/0122802 | A1* | 5/2016 | Frayling | C12Q 1/6806 506/40 |
| 2018/0333724 | A1 | 11/2018 | Hull et al. | |
| 2019/0250102 | A1 | 8/2019 | Iizuka et al. | |
| 2019/0285579 | A1 | 9/2019 | Iizuka et al. | |
| 2020/0116709 | A1 | 4/2020 | Konry et al. | |
| 2023/0160850 | A1* | 5/2023 | Cumming | G01N 33/54373 204/406 |

OTHER PUBLICATIONS

Baret, J. L., "Surfactants in droplet-based microfluidics," Lab on a Chip, 12(3), pp. 422-433 (2012), DOI: 10.1039/C1LC20582J, 37 pages.
Feng et al., "MRBLES 2.0: High-throughput generation of chemically functionalized spectrally and magnetically encoded hydrogel beads using a simple single-layer microfluidic device," Microsystems & Nanoengineering, vol. 6, Article No. 109 (2020), DOI: 10.1038/s41378-020-00220-3, 13 pages.
Glenn et al., "High-resolution magnetic resonance spectroscopy using a solid-state spin sensor," Nature 555 (7976):351-354 (2018), DOI: 10.1038/nature25781, abstract.
Hatch et al., "Tunable 3D droplet self-assembly for ultra-high-density digital micro-reactor arrays," Lab on a Chip, 11, 2509-2517 (2011), DOI:10.1039/C0LC00553C, 9 pages.
Parthiban et al., "Self-assembly of droplets in three-dimensional microchannels," Soft Matter, 15, 4244-4254 (2019), DOI: 10.1039/C8SM02305K, 11 pages.
Schirhagl et al., "Nitrogen-Vacancy Centers in Diamond: Nanoscale Sensors for Physics and Biology," Annu. Rev. Phys. Chem., 65:83-105 (2014), DOI: 10.1146/annurev-physchem-040513-103659, 27 pages.
Stanley et al., "A microfluidic approach for high-throughput droplet interface bilayer (DIB) formation," Chemical Communications, 46(10), 1620-1622 (2010), DOI: 10.1039/B924897H, 5 pages.
Yang et al., "Amperometric Electrochemical Microsystem for a Miniaturized Protein Biosensor Array," IEEE Transactions on Biomedical Circuits and Systems, vol. 3, No. 3, pp. 160-168 (2009), 9 pages.
Zhang et al., "Selective addressing of solid-state spins at the nanoscale via magnetic resonance frequency encoding," npj Quantum Inf. 3:31 (2017), 8 pages.
Zhang et al., "High-Density Droplet Microarray of Individually Addressable Electrochemical Cells," Anal. Chem. 2017, 89, 11, 5832-5839 (Abstract only), 1 page.
Cole et al., "Multiplexed electrical sensor arrays in microfluidic networks," Sensors and Actuators B: Chemical 136:350-358 (2009), 9 pages.
Curk et al., "Rational Design of Molecularly Imprinted Polymers," Soft Matter (2015), DOI: 10.1039/C5SM02144H, 29 pages.
Glenn et al., "High-resolution magnetic resonance spectroscopy using a solid-state spin sensor," Nature 555:351 (2018), 14 pages.
Guan et al., "A highly parallel microfluidic droplet method enabling single-molecule counting for digital enzyme detection," Biomicrofluidics 8:014110 (2014), 14 pages.
Hatch et al., "1-Million droplet array with wide-field fluorescence imaging for digital PCR," Lab Chip 11:3838 (2011), 8 pages.
Hess et al., "High-throughput, Quantitative Enzyme Kinetic Analysis in Microdroplets Using Stroboscopic Epifluorescence Imaging," Analytical Chemistry (2015), DOI: 10.1021/acs.analchem.5b00766, 8 pages.
Hu et al., "Versatile microfluidic droplets array for bioanalysis," ACS Applied Materials & Interfaces: Just Accepted Manuscript [online] Retrieved from the Internet <URL:http://pubs.acs.org> [downloaded on Dec. 23, 2014], DOI: 10.1021/am5075216 (2014), 2—pages.
Huebner et al., "Static microdroplet arrays: a microfluidic device for droplet trapping, incubation and release for enzymatic and cell-based assays," Lab Chip 9:692-698 (2009), 7 pages.
Jammes et al., "How single-cell immunology is benefiting from microfluidic technologies," Microsystems & Nanoengineering 6:45 (2020), 14 pages.
Lim et al., "Micro-optical lens array for fluorescence detection in droplet-based microfluidics," Lab Chip (2013), DOI: 10.1039/c3lc41329b, 4 pages.
Lim et al., "Ultra-high throughput detection of single cell ß-galactosidase activity in droplets using micro-optical lens array," Applied Physics Letters 103:203704 (2013), 5 pages.
Malara et al., "A self-operating broadband spectrometer on a droplet," Nature Communications 11:2263 (2020), 5 pages.
Meier et al., "On-chip monitoring of chemical syntheses in microdroplets via surface-enhanced Raman spectroscopy," Chem Comm 51:8588-8591 (2015), 5 pages.
Patra et al., "Time-Resolved Non-Invasive Metabolomic Monitoring of Microfluidic Spheroid and Monolayer Cell Cultures by NMR," School of Chemistry, Univ of Southampton, United Kingdom (2020), 14 pages.
Sarkar et al., "Dynamic analysis of immune and cancer cell interactions at a single cell level in microfluidic droplets," Biomicrofluidics 10:054115 (2016), 13 pages.
Schmitz et al., "Dropspots: a picoliter array in a microfluidic device," Lab Chip 9:44-49 (2009), 7 pages.
Schonbrun et al., "High-throughput fluorescence detection using an integrated zone-plate array," Lab Chip 10:852-856 (2010), 5 pages.
Symes et al., "Cavity enhanced droplet spectroscopy: Principles, perspectives and prospects," Phys. Chem. Chem. Phys 6:474-487 (2004), 14 pages.
Tonooka et al., "Lipid Bilayers on a Picoliter Microdroplet Array for Rapid Fluorescence Detection of Membrane Transport," Small 10(16):3275-3282 (2014), 8 pages.
Zhang et al., "High-Density Droplet Microarray of Individually Addressable Electrochemical Cells," Analytical Chemistry: Just Accepted Manuscript [online] Retrieved from the Internet <URL:http://pubs.acs.org> [downloaded May 12, 2017] (2017), 10 pages.

* cited by examiner

PARALLELIZED PROBING OF A PLURALITY OF SAMPLES IN A SELF-ORGANIZED STRUCTURE

CROSS-REFERENCE TO RELATED APPLICATIONS

This application is the national phase entry of International Patent Application No. PCT/EP2022/063262, filed May 17, 2022, and claims the benefit of European Patent Application No. 21174441.2, filed May 18, 2021, the disclosures of which are incorporated herein by reference in their entirety.

FIELD OF THE INVENTION

The present invention is in the field of chemical analysis and medical diagnostics. In particular, the invention relates to a method for parallelized probing of a plurality of samples, a corresponding sensor chip, a corresponding sensing device, and a corresponding measurement system.

BACKGROUND

High-throughput parallelized analysis of samples is essential for many applications in chemistry, life sciences, and medicine. Such experiments may for example be conducted on standardized microplates, which typically comprise a rectangular array of wells for receiving the samples and due to their standardized well layout allow for an efficient processing of a large number of samples using liquid handling robots.

To further increase throughput, microfluidic chips have been developed that comprise a plurality of sample sites such as microfluidic sample wells, in which samples may be provided and processed simultaneously. The sample wells typically have a size on the order of 10 μm to 100 μm, which not only allows for placing a large number of sample wells on a single chip, but also facilitates arranging sensors in close proximity to the samples. The sensors may be integrated in the chip and may for example be configured to measure a temperature or electric or magnetic properties of the samples, see. e.g. C. Yang et al., *IEEE Transactions on Biomedical Circuits and Systems*, vol. 3, no. 3, pp. 160-168 (2009), H. Zhang et al., *Anal. Chem.* 2017, 89, 11, 5832-5839 and H. Zhang et al., npj *Quantum Inf.* 3:31 (2017). In other examples, the samples may be probed by optical means such as fluorescence spectroscopy.

However, while such microfluidic chips enable rapid probing of a large number of samples in parallel, the small size of the sample wells causes a number of challenges for fabrication and in particular for handling of the chips. The microfluidic chips are prone to mechanical damage as well as contamination from previous samples as it is next to impossible to completely remove samples from the sample wells after a measurement. As a result, the microfluidic chips are typically single-use products, which makes the experiments costly and also timeconsuming since a new chip may have to be mounted and possibly re-aligned for each experiment. Moreover, preparing the samples in the sample wells is difficult due to the small length scales involved. Owing to the tiny volumes of the sample wells, samples may also evaporate during the preparation and measurement, which may reduce the reliability of the results from the measurement.

US 2019/0285579 A1 discloses a fluorescent testing system with a dielectrophoresis device. The dielectrophoresis device comprises microwells, in which test objects such as cells can be arranged above a corresponding photodiode. Using a pair of electrodes, a test object can be captured in one of the microwells by means of dielectrophoresis.

A similar device is also known from US 2019/0250102 A1.

SUMMARY OF THE INVENTION

The object of the invention is thus to simplify sample preparation and sample handling for high-throughput parallelized probing of a plurality of samples on microfluidic sensor chips.

This object is met by a method for parallelized probing of a plurality of samples, a sensor chip for parallelized probing of a plurality of samples, a sensing device for parallelized probing of a plurality of samples, and a measurement system for parallelized probing of a plurality of samples according to the claims. Embodiments of the present invention are detailed in the dependent claims.

The method for parallelized probing of a plurality of samples according to the invention comprises providing a sensor chip, wherein the sensor chip comprises a sensing layer arranged in or on a substrate and a measurement volume adjacent to the sensing layer. The sensing layer comprises a plurality of sensing elements, each of which is configured to generate a sensor signal characterizing a physical observable in the vicinity of the respective sensing element. A carrier fluid comprising a plurality of sample objects is provided to the measurement volume, wherein each of the sample objects comprises or forms a respective sample. A number of sample objects in the measurement volume is controlled such that the sample objects form a self-organized structure in the measurement volume. A measurement is performed on one or more of the samples while the sample objects are arranged in the self-organized structure, wherein a measurement on a sample is performed using one or more sensing elements arranged adjacent to the respective sample object in the self-organized structure.

The sensor chip may comprise a single-layer or multilayer substrate, wherein the measurement volume may for example be a recess in a top surface of the substrate or a hollow volume enclosed by the substrate. In addition, the sensor chip may comprise microfluidic structures such as an inlet channel and/or an outlet channel that are in fluid communication with the measurement volume to provide the carrier fluid thereto. In some examples, the sensor chip may be a sensor chip according to any one of the embodiments of the present invention described herein or a sensor chip of a sensing device according to any one of the embodiments of the present invention described herein.

Each of the sensing elements is configured to generate a sensor signal, e.g. an optical, magnetic, and/or electrical signal, that characterizes a physical observable in the vicinity of the sensing element, e.g. at the position of the sensing element or in a sensing volume around the sensing element. In the context of this disclosure, a sensing element may refer to any element or unit that may be used for reading out a sensor signal that allows for measuring or quantifying the respective physical observable. The sensing elements may for example comprise one or more of a capacitive, inductive, and/or resistive sensing element such as a microelectrode, a thermistor or a microelectromechanical system (MEMS), a piezoelectric sensing element, a Hall-effect sensing element, and a photosensitive sensing element such as a photodiode, wherein the sensor signal may for example be an electric current or voltage. In some embodiments, some or all of the sensing elements may be atomic- or molecular-scale sensing elements, e.g. atomic- or molecular-scale structures having an optical absorption and/or emission spectrum that depends on the physical observable, wherein the sensor signal may for example be a transmitted light intensity or an emitted light intensity. The sensing elements may in particular be solid-state spin systems, for example as detailed below.

The physical observable may be any measurable physical quantity, for example a temperature, a pH value, an electrical conductivity, a permittivity, an electric field, a magnetic field, and/or a light intensity. Each of the sensing elements may be configured to measure the same physical observable or at least some of the sensing elements may be configured to measure different physical observables. In some examples, the sensing elements may be configured to measure a first physical observable, e.g. at the position of the respective sensing element, which in turn may depend on a second physical observable, e.g. the same or a different physical observable at a different position or within a sensing volume around the sensing element, in particular a position or sensing volume within the measurement volume. Accordingly, the sensor signals of the sensing elements may also characterize the second physical observable in addition to the first physical observable.

The sensing elements may be distributed throughout the sensing layer, e.g. homogenously with a uniform density and/or a uniform spacing between adjacent sensing elements, or may be confined to spatially separated regions within the sensing layer, e.g. as detailed below. An ensemble of adjacent sensing elements within a region or portion of the sensing layer may be referred to as a sensing region in the following. The sensing elements in a given sensing region may be spatially separated from other sensing elements in the sensing layer or may be a subset of sensing elements selected from sensing elements that are distributed throughout the sensing layer, e.g. the sensing elements within a selected region or portion of the sensing layer, which may not be spatially separated from other sensing elements in the sensing layer.

In some embodiments, the sensing elements may form a plurality of sensors. Each of the sensors may comprise one or more sensing elements, for example an ensemble of sensing elements that are configured to generate a common sensor signal, wherein the common sensor signal may e.g. be a sum or an average of the sensor signals of the sensing elements in the ensemble. The sensors may be spatially separated and/or may be configured to be read out independently from the other sensors. In some embodiments, each of the sensors may comprise the sensing elements within a respective sensing region, wherein the sensing regions may be spatially separated from each other, i.e. each sensor may correspond to one of a plurality of spatially separated sensing regions in the sensing layer. In some examples, some or all of the sensor may only comprise a single sensing element.

In some embodiments, performing the measurement on the one or more samples may comprise, for each of the one or more samples, selecting a subset of the sensing elements and selectively determining sensor signals from the sensing elements in the respective subset. For example, sensor signals may only be determined for sensing elements in subsets associated with the one or more samples on which a measurement is to be performed. The sensing elements in the subset for a given sample may for example be arranged in a sensing region, in particular a sensing region adjacent to the respective sample object in the self-organized structure. The subset may for example comprise all sensing elements in the respective sensing region. For sensing elements outside of the sensing regions associated with the one or more samples on which a measurement is to be performed, i.e. sensing elements in other portions of the sensing layer, no sensor signals may be determined.

Selecting the subset of the sensing elements and selectively determining the sensor signals from the sensing elements in the subset, e.g. in the respective sensing region, may comprise selectively activating the sensing elements in the subset and/or selectively reading out the sensing elements in the subset. For example, only sensing elements in sensing regions associated with the one or more samples on which a measurement is to be performed may be activated and/or read out. Activating a sensing element may for example comprise changing a state of the sensing element, e.g. from an off-state, in which the sensing element does not generate a sensor signal, to an on-state, in which the sensing element generates a sensor signal. A sensing element may for example be activated electrically, e.g. using an electrical switch, and/or optically, e.g. by optically exciting the sensing element. Selectively reading out the sensing elements in the subset may for example comprise measuring sensor signals only for sensing elements in the respective subset or discarding sensor signals for sensing elements that are not contained in the respective subset, e.g. when processing or analyzing the measured sensor signals.

In some embodiments, the sensing elements in the sensing layer form an array of spatially separated sensors, wherein each of the sensors comprises one or more sensing elements. In the self-organized structure, a respective sample object may be arranged adjacent to each of the sensors in the array and a measurement on a sample may be performed using the respective sensor. In some examples, the sensors in the array may be spatially separated sensing regions, each of which comprises a plurality of sensing elements.

The sensors may be arranged in a one-dimensional array, in which the sensors may e.g. be arranged along a first direction with a spacing between adjacent sensors, or in a two-dimensional array, in which the sensors may e.g. be arranged in a plane with a spacing between adjacent sensors. In some embodiments, the sensor array may be a periodic array. The sensors may for example be arranged in a one-dimensional periodic array, in which the sensors may e.g. be positioned at an equidistant spacing along the first direction. Preferably, the sensors are arranged in a two-dimensional periodic array, in which the sensors may e.g. be positioned at a first equidistant spacing in the first direction and at a second equidistant spacing in a second direction. The second spacing may be the same as the first spacing or may be different. Preferably, all sensors of the array are arranged in a common plane, which may be parallel to a wall of the measurement volume. The sensing elements may for example be embedded in a bottom or top wall of the measurement volume, wherein a surface of each sensing element may be exposed to the measurement volume. In other examples, the sensing elements may be fully embedded in the bottom or top wall such that the sensing elements are not exposed to the measurement volume. Each sensor may be associated with a respective unit cell of the array, wherein a unit cell is the fundamental unit that the array is formed of by successive tiling or translation of identical unit cells. A unit cell of the array may for example be the area that is closer to a given sensor than to any other sensor of the array.

In a preferred embodiment, a physical dimension of each sample object corresponds to a spacing of the sensor array, i.e. the pitch or center-to-center distance between adjacent sensors in the senor array along the first and/or second direction. The sample objects may for example be monodisperse objects with a diameter or a width corresponding to the first and/or second spacing of the sensor array. For this, a spacing of the sensor array may be chosen such that the spacing of the sensor array corresponds to a physical dimension of the sample objects, e.g. when probing sample objects of a predetermined size such as cells or beads. In other words, the sensor chip that is provided may be adapted to the physical dimension of the sample objects. Alternatively, a physical dimension of the sample objects may be chosen such that the physical dimension of the sample objects corresponds to the spacing of the sensor array, e.g. when probing sample objects with an adjustable size such as microdroplets. For example, a flow velocity of the carrier fluid and/or of a sample fluid in a droplet generator, a viscosity of the carrier fluid and/or of the sample fluid, and/or a surface tension at the carrier fluid-sample fluid interface may be adjusted to adapt the physical dimension of the microdroplets to the spacing of the sensor array. In some embodiments, the physical dimension of the sample objects may be larger than a physical dimension of the sensors or sensing regions. A diameter or a width of the sample objects may for example be at least 50%, in some examples at least oo % larger than a diameter or a width of the sensors or sensing regions.

The sample objects may for example be microdroplets that are dispersed in the carrier fluid. The microdroplets may for example comprise or consist of a sample fluid, wherein the sample fluid may for example be a biological sample fluid, which may e.g. comprise biological samples such as proteins, DNA, bacteria, cells or parts thereof, or a chemical sample fluid, which may e.g. comprise one or more reagents and/or products of a chemical reaction. The microdroplets may have a well-defined shape, e.g. a spherical shape, in the carrier fluid, for example due to the surface tension at the interface between the microdroplet and the carrier fluid, which may also prevent the microdroplets from merging when coming in contact with each other. In some examples, the microdroplets may be monodisperse microdroplets, i.e. may have the same diameter or width. In other embodiments, the sample objects may also be other objects, in particular cells or constituents thereof, solid microparticles, or microbubbles. The sample objects may for example be microbeads, e.g. agarose beads, or magnetic microparticles.

In some examples, the sample fluid and the carrier fluid may be immiscible, wherein the sample fluid may e.g. be an aqueous solution and the carrier fluid may e.g. comprise a hydrophobic fluid such as an oil. Preferably, the carrier fluid comprises one or more of toluene, chloroform, methanol, dimethyl sulfoxide (DMSO), and tetrahydrofuran (THF). The carrier fluid and the microdroplets may form an emulsion with the carrier fluid being the continuous phase and the sample fluid being the dispersed phase. Additionally or alternatively, the carrier fluid and/or the sample objects may comprise surfactants such as amphiphilic molecules, e.g. to stabilize the microdroplets in the carrier fluid. The microdroplets may for example comprise a shell layer formed by the surfactants, which may e.g. enclose a core comprising the sample fluid. In some examples, the microdroplets are vesicles or liposomes having a lipid bilayer that encloses a core formed by the sample fluid.

The carrier fluid comprising the plurality of sample objects is provided to the measurement volume, e.g. by pipetting into the measurement volume or through an inlet channel of the sensor chip. The number of sample objects in the measurement volume is controlled such that the sample objects form a self-organized structure in the measurement volume. For this, the number of sample objects in the measurement may be adjusted, e.g. by providing additional sample objects to the measurement volume or removing sample objects from the measurement volume. This may for example comprise continuously providing the carrier fluid comprising the sample objects to increase the number of sample objects in the measurement volume until the self-organized structure forms. In some embodiments, this may also comprise releasing carrier fluid from the measurement volume without removing sample objects therefrom, e.g. by pipetting or through an outlet channel having a cross-sectional area that is smaller than a cross-sectional area of the sample objects.

In the context of this disclosure, a self-organized structure of sample objects refers to a structure in which the arrangement of the sample objects is at least in part defined by interactions between the sample objects themselves, e.g. by repulsive and/or attractive surface-surface interactions between sample objects that are in contact or close proximity to each other. In some embodiments, interactions between the sample objects may be mediated by the carrier fluid at least in part. The interaction with adjacent sample objects may prevent motion of a given sample object within the self-organized structure. In other words, the position of a given sample object in the self-organized structure may not or at least not only be determined by structural features of the sensor chip. In some embodiments, the self-organized structure may be periodic, e.g. such that adjacent sample objects are positioned at an equidistant spacing in one or two directions.

In the self-organized structure that is formed in the measurement volume, the sample objects may for example be arranged such that a respective sample object is adjacent to each of the sensors in the sensor array. For example, the sample object may be aligned with the unit cell associated with the respective sensor. In some examples, a center of the sample object may be aligned with a center of the respective sensor, e.g. such that a distance between the center of the sample object and the center of the respective sensor is minimal. In some examples, the sample object may be in contact with a surface of the respective sensor or with a surface of a wall portion of the measurement volume that is closest to the respective sensor. Preferably, each of the sample objects is arranged adjacent to a respective sensor. The self-organized structure may for example have the same structure as the sensor array, i.e. the sample objects may be arranged in the same pattern as the sensors. In some embodiments, the self-organized structure may be periodic and may have the same lattice structure as the sensor array, i.e. the sample objects may be arranged in the same periodic pattern as the sensors, e.g. such that each of the sample objects is aligned with a respective one of the unit cells of the array.

In other embodiments, the sample objects in the self-organized structure may be arranged such that some or all of the sample objects are arranged adjacent to a respective sensing region in the sensing layer, wherein each sensing region may for example contain the sensing elements of the subset of sensing elements selected for the respective sample. In other words, the arrangement of the sample objects in the self-organized structure may be adapted to the arrangement of the selected subsets or sensing regions in the sensing layer or vice versa. In some examples, the sensing regions may be predetermined sensing regions, which may e.g. be defined by structural features of the sensor chip such as a distribution of the sensing elements in the sensing layer or may have been selected prior to formation of the self-organized structure, and the sample objects in the self-organized structure may be arranged such that some or all of the sample objects are arranged adjacent to a respective predetermined sensing region.

After the self-organized structure is formed, a measurement is performed using some or all of the sensing elements in the sensing layer while the sample objects are arranged in the self-organized structure. A measurement on a sample may for example be performed using the sensing elements of the sensing region or sensor associated with the respective sample. Preferably, the sample objects do not move while the measurement is performed, i.e. the self-organized structure may be stationary during the measurement. In some examples, this may comprise interrupting a flow of the carrier fluid through the measurement volume.

By preparing a self-organized structure in the measurement volume, the sample objects may be arranged adjacent to corresponding sensing regions or sensors without requiring individual structural features such as sample wells or hydrophilic or hydrophobic surface coatings for each of the sensing regions or sensors. Instead, a small number of boundary or guiding structures such as sidewalls of the measurement volume may be used to globally define the position of the self-organized structure relative to the sensing regions or the sensor array. This may for example allow for using a measurement volume with flat wall surfaces, which greatly facilitates manufacturing of the sensor chip as well as the handling thereof. In particular, the measurement volume can be cleaned more easily than individual sample wells, which may allow for re-using a sensor chip multiple times without risk of contamination. This not only reduces costs, but also increases throughout as the sensor chip does not have to be exchanged between measurements. Furthermore, no positioning of individual sample objects, e.g. by targeted pipetting, is required, which simplifies the preparation of the samples on the sensor chip. The proposed method can thus be automated easily and enables a fast and cost-efficient parallel probing of a large number of samples.

Microdroplets arranged in periodic structures have previously for example been used to increase the density of microdroplets used as microreactors in an imaging plane of a microscope, see US 2012/0184464 A1 and A. C. Hatch et al, *Lab Chip,* 2011, 11, 2509. Similar methods for forming microdroplet arrays in microfluidic structures are for example known from C. E. Stanley et al., *Chem. Commun.,* 2010, 46, 1620-1622 and P. Parthiban et al., *SoftMatter,* 2019, 15, 4244-4254.

The sensor chip may comprise boundary or guiding structures that are configured to confine or guide a motion of the sample objects within the measurement volume. The boundary or guiding structures, collectively referred to as boundary structures in the following, may for example comprise one or more of a sidewall of the measurement volume, a guiding wall protruding from a bottom and/or top wall of the measurement volume, and/or a hydrophilic and/or hydrophobic coating on the bottom and/or top wall of the measurement volume, e.g. as detailed below. The self-organized structure may be formed by interactions between the sample objects and the boundary structures as well as by surface-surface interactions between the sample objects. Interactions between the sample objects and the boundary structures may for example be direct interactions of the boundary structures with the sample objects themselves or may be mediated by the carrier fluid. The boundary structures may be arranged or shaped such that the self-organized structure is aligned relative to the sensing regions or the sensor array, e.g. as described below for the sensor chip according to the invention and the sensing device according to the invention. For this, the boundary structures may for example be placed at a distance corresponding to one half of a spacing of the sensor array from the outermost sensors in the array. The boundary structures may for example be aligned with edges of unit cells of the sensor array, e.g. such that an edge of each of the outermost unit cells of the sensor array is aligned with one of the boundary structures.

In the self-organized structure, the interactions between the sample objects and the boundary structures and the surface-surface interactions between the sample objects may prevent sample objects from moving, thus pinning sample objects to predetermined positions, which may e.g. be adjacent to the respective sensors or sensing regions. In other words, it may not be possible to move a given sample object without moving at least one other sample object, e.g. because the respective sample objects are in contact. Preferably, the self-organized structure is formed such that at least 90%, in some examples at least 95% of the sample objects are prevented from moving along two or more orthogonal directions, e.g. in a plane parallel to the bottom or top wall of the measurement volume. This may be sufficient to prevent the entire self-organized structure from moving or disintegrating during the measurement. In some examples, sample objects in the self-organized structure that are arranged adjacent to an inlet or outlet of the measurement volume may still be able to move in one or more directions without moving other sample objects.

In some embodiments, the sample objects may have a circular cross section. The sample objects may for example have a spherical, spheroidal, ellipsoidal or cylindrical shape. The self-organized structure may be a close-packing of circles, e.g. when projected or viewed along a direction perpendicular to the sensing layer and/or a wall of the measurement chamber adjacent to the sensing layer. In the close-packing of circles, the sample objects may be arranged in a single layer such that their circular circumferences are in contact or close proximity to each other, thus preventing the sample objects from moving. The close-packing of circles may correspond to the densest possible arrangement of the sample objects under the boundary conditions imposed by the boundary structures in the measurement volume.

In some embodiments, the sample objects in the self-organized structure may not have a circular cross section, but the self-organized structure may nonetheless resemble a close-packing of circles, e.g. in the sense that centers of the sample objects and/or contact points between the sample objects are aligned with the corresponding points in an ideal close-packing of circles. A circumference of a sample object in the self-organized structure may for example be tangential to a circle in the close-packing of circles (or vice-versa) at points at which the sample object is in contact or close proximity with adjacent sample objects. A physical dimension of the sample objects may for example be equal to a diameter of the circles in the close-packing. The sample objects may have a non-circular cross-section intrinsically, e.g. when being provided in the carrier fluid, and/or may deform when forming the self-organized structure, e.g. when coming in contact with adjacent sample objects and/or boundary structures of the sensor chip.

The self-organized structure may in particular be a close-packing of equal circles, i.e. a close-packing of circles having the same diameter. All of the sample objects may e.g. have a circular cross section with the same diameter. Accordingly, some or all of the sample objects may for example be arranged in a two-dimensional hexagonal lattice in the self-organized structure, i.e. such that each sample object is surrounded by six equidistant neighboring sample objects, thereby forming a self-organized periodic structure. The two-dimensional hexagonal lattice corresponds to the close-packing of equal circles in a uniform space, which may also be referred to as a uniform close-packing of equal circles in the following. In other examples, some or all of the sample objects may be arranged in a linear chain in the self-organized structure, wherein each sample object is in contact with two neighboring sample objects.

In some examples, the sample objects may have a spherical shape and the self-organized structure may be a close-packing of spheres, in particular a close-packing of equal spheres, i.e. may correspond to the densest possible arrangement of spheres under the boundary conditions imposed by the boundary structures in the measurement volume. The sample objects in the self-organized structure may be arranged in a single layer, e.g. in a single plane, wherein the close-packing of spheres in a single layer corresponds to a close-packing of circles when projected in a direction perpendicular to the layer.

In some embodiments, the carrier fluid comprising the sample objects may be provided through a microfluidic inlet channel that is in fluid communication with the measurement volume. Controlling the number of sample objects in the measurement volume may comprise maintaining a flow of the carrier fluid comprising the sample objects through the inlet channel until the self-organized structure is formed. In this way, sample objects may be added to the measurement volume successively until the self-organized structure is formed. In some examples, this may comprise releasing carrier fluid from the measurement volume, e.g. via a microfluidic outlet channel, while preventing sample objects from leaving the measurement volume, e.g. by using an outlet channel with a width or a cross-sectional area that is smaller than a width and a cross-sectional area, respectively, of the sample objects or by adjusting the width or the cross-sectional area of the outlet channel accordingly, e.g. using a valve.

In a preferred embodiment, the method further comprises tracking a motion of one or more sample objects on the sensor chip, for example prior to and/or after performing a measurement on the respective sample. Tracking a motion of a sample object may for example comprise determining a point in time at which the sample object reaches one or more pre-determined points on the sensor chip, for example an inlet of the measurement volume, an outlet of the measurement volume, and/or an output port of the sensor chip. Tracking the motion of the sample object may further comprise associating the sample object with the respective sensor or sensing elements, e.g. to associate the sample object with a measurement result obtained from the respective sensor or sensing elements. Additionally or alternatively, tracking the motion of the sample object may also comprise associating the sample object and/or the measurement result with information pertaining to a composition and/or a formation process of the sample object. The sample objects may for example be formed with a composition and/or other properties that vary over time, e.g. using a droplet generator. Tracking the motion of the sample object may allow for associating the sample object and/or the measurement result with a point in time at which the respective sample object was formed, with a certain composition, e.g. a concentration of a sample substance, and/or certain parameters used for forming the sample object, e.g. a flow velocity, a fluid composition, and/or a temperature in the droplet generator. The motion of a sample object may for example be tracked based on a flow velocity of the carrier fluid, a duration of a flow of the carrier fluid, and/or a position of the respective sensor or sensing elements. In a preferred embodiment, the motion of one or more sample objects on the sensor chip is tracked continuously, e.g. by determining a position of the sample object on the sensor chip at a plurality of points in time. The one or more sample objects may for example be tracked using a camera that is configured to record images of the sample objects on the sensor chip. Tracking the sample objects on the sensor chip may for example allow for a sorting of sample objects based on the respective measurement results. In some examples, the sample objects may comprise a marker that allows for distinguishing the sample objects from each other, for example by spectroscopic means, e.g. as described in Y. Feng et al., *Mi-crosystems & Nanoengineering* Vol. 6, 109 (2020).

In a preferred embodiment, the sensing elements are magnetic quantum sensing elements, e.g. atomic- or molecular-scale structures exhibiting a magnetic field-dependent behavior, for example a magnetic field-dependent energy spectrum and/or magnetic-field dependent transition rates between different states of the magnetic quantum sensing element. The sensing elements may in particular be optically addressable solid-state spin systems. Optically addressable solid-state spin systems are quantum systems with a spin degree of freedom that are arranged or embedded in a solid host material, wherein the spin degree of freedom can be read out and/or manipulated via optical transitions and/or a microwave field. The spin systems may in particular be objects that behave like artificial atoms or molecules, i.e. systems that exhibit an atom- or molecule-like energy spectrum and have at least two different spin states. The spin systems may for example be optically active defects in a crystal structure. Energy levels of different spin states may shift in the presence of a magnetic field. Furthermore, a spin system may for example have a spin-state dependent transition rate between different states of the spin system, e.g. electronic states of the spin system. The solid-state spin systems may thus be used as a probe for a magnetic field, e.g. by determining an energy difference and/or a transition rate between states of the spin systems. In a preferred embodiment, the substrate comprises or consists of diamond and the solid-state spin systems are diamond color centers, i.e. optically active point defects in the diamond crystal structure. Preferably, the spin systems are nitrogen-vacancy (NV) centers in diamond, in particular negatively charged nitrogen-vacancy centers.

Performing a measurement on a sample may comprise illuminating the solid-state spin systems arranged in a sensing region adjacent to the respective sample object in the self-organized structure with light to optically excite the solid-state spin systems in the sensing region and detecting an optical signal emitted by the solid-state spin systems in the sensing region.

Preferably, solid-state spin systems in some or all of the sensing regions are excited simultaneously by illuminating the sensing regions with light propagating along an optical illumination path through the sensor chip that connects some or all of the sensing regions, i.e. such that a light pulse propagating along the illumination path sequentially passes through the respective sensing regions. A wavelength of the light may e.g. be tuned to an absorption wavelength of the spin systems. The illumination of the sensing regions along the illumination path may in particular be used to optically polarize the spin systems in the sensing regions and/or to excite the spin systems in the sensing regions to induce the optical signals to be detected, i.e. for optical read-out. An intensity and/or a pulse duration of the light pulses may for example be chosen such that the spin systems are prepared in a pre-defined quantum state. In some examples, the intensity and/or pulse duration may be chosen such that spin systems in the sensors undergo multiple transitions, e.g. to increase a fluorescence intensity and/or for optical polarization of the spin systems, i.e. to optically pump the spin systems to a pre-defined state. In a preferred embodiment, the sensing regions are illuminated multiple times, e.g. a first time for optical polarization and a second time for inducing the optical signal to be detected. At least one of the illuminations, preferably both of the illuminations occur by light propagating along the illumination path.

The optical signals may be detected simultaneously, e.g. using a multi-channel photodetector. The optical signal may for example be the intensity of light emitted by the spin systems at one or more emission wavelengths, e.g. fluorescence emitted by excited spin systems, or may be the intensity of light transmitted through the sensing regions, e.g. to determine an absorption rate of light at one or more absorption wavelengths by the spin systems. The detected signal may for example allow for extracting information pertaining to the state of the spin systems, e.g. an occupation probability of one or more spin states, which in turn may for example be used to extract information pertaining to a strength and/or orientation of a magnetic field at the respective sensor, which may e.g. originate from the corresponding sample at least in part.

The invention further provides a sensor chip for parallelized probing of a plurality of samples using a method according to any one of the embodiments described herein. The sensor chip comprises a measurement volume configured to receive a carrier fluid comprising a plurality of sample objects. The sensor chip further comprises an array of sensors that are arranged in or adjacent to a first wall of the measurement volume, wherein the sensor array has a first spacing $a_1$. Each of the sensors comprises one or more sensing elements, each of which is configured to generate a sensor signal characterizing a physical observable in the vicinity of the respective sensing element. The sensor chip comprises two or more boundary or guiding structures that are configured to confine or guide a motion of the sample objects in the measurement volume. The two or more boundary or guiding structures are arranged such that when a close-packing of solid objects having a circular cross section with a diameter equal to the first spacing $a_1$ is placed in the measurement volume with the close-packing of the solid objects covering the entire first wall of the measurement volume, the two or more boundary or guiding structures confine the solid objects such that a respective solid object is aligned with each of the sensors.

The sensor chip may comprise a single-layer or multilayer substrate, wherein preferably the substrate or at least a part thereof is optically transparent in the ultra-violet, visible, and/or near-infrared spectrum. The measurement volume may for example be a recess in a top surface of the substrate or a hollow volume enclosed by the substrate. In some embodiments, the sensor chip may comprise a removable cover for opening and closing the measurement volume. In addition, the sensor chip may comprise microfluidic structures such as an inlet channel and/or an outlet channel that are in fluid communication with the measurement volume to provide or release the carrier fluid to/from the measurement volume. The sensor chip may also comprise a droplet generator, e.g. as detailed below. The first wall may for example be a bottom wall or a top wall of the measurement volume, which may for example be formed by the substrate and/or by the removable cover. Preferably, the first wall has a flat surface and does not comprise any protrusions and/or depressions. In some examples, a surface of the sensors and/or a surface of the sensing elements may be exposed to the measurement volume and may e.g. be flush with a surface of the first wall. In other examples, the sensors and/or the sensing elements may be fully embedded in the first wall or in another layer below the first wall and may not be exposed to the measurement volume. In some embodiments, each of the sensors may comprise sensing elements within a respective sensing region, e.g. as detailed above. The sensing elements may be confined to a plurality of spatially separated sensing regions, for example in a sensing layer in or adjacent to the first wall, with the sensing regions being arranged in an array, thereby forming the array of sensors.

The sensors may be arranged in a one-dimensional array or a two-dimensional array. The sensors may be arranged in a one-dimensional periodic array, in which the sensors may e.g. be positioned at an equidistant spacing $a_1$ along a first direction. Alternatively, the sensors may be arranged in a two-dimensional periodic array, in which the sensors may e.g. be positioned at a first equidistant spacing $a_1$ in the first direction and at a second equidistant spacing $a_2$ in a second direction. In the following, the first spacing or the second spacing may also be referred to as a spacing $a_0$ of the sensor array. Accordingly, any reference to the spacing $a_0$ is to be understood as referring to the first spacing for a one-dimensional array and to either the first spacing $a_1$ or the second spacing $a_2$ for a two-dimensional array.

Preferably, all of the sensors are arranged in the same plane, which may e.g. be parallel to the first wall. The sensors may for example be arranged in a sensing layer in or on a substrate of the sensor chip adjacent to the measurement volume. Each sensor may be associated with a respective unit cell of the array, wherein a unit cell is the fundamental unit that the array is formed of by successive tiling or translation of identical unit cells. In one example, the sensors are arranged in a two-dimensional hexagonal lattice, i.e. such that each sensor is surrounded by six equidistant neighboring sensors. Accordingly, the unit cell of the array may for example be a hexagon, wherein the edges of a unit cell associated with a given sensor are defined by the perpendicular bisectors of the vectors connecting the sensor to its neighboring sensors. In another example, the sensors are arranged in a two-dimensional rectangular lattice, wherein the unit cell of the array has a rectangular shape. In yet another example, the sensors are arranged in a one-dimensional equidistant chain, wherein the unit cell may for example be defined as a square around a given sensor with a size of the square corresponding to the spacing $a_0$ between adjacent sensors.

The boundary or guiding structures, collectively referred to as boundary structures in the following, may for example comprise one or more sidewalls of the measurement volume, wherein each of the sidewalls extends under an angle to the first wall, preferably under an angle of more than 60°. The sidewalls may in particular be perpendicular to the first wall. Preferably, some or all of the sidewalls of the measurement volume have flat surfaces, i.e. do not comprise any angled portions, protrusions, and/or depressions. Additionally or alternatively, the boundary structures may comprise one or more guiding walls that protrude from the first wall of the measurement volume and/or from a second wall of the measurement volume opposing the first wall. The boundary structures may further comprise one or more hydrophilic and/or hydrophobic coatings on the first and/or second wall of the measurement volume, wherein the coatings may for example define an area on the first wall that can be wetted by the carrier fluid or an area of the first wall that cannot be wetted by the carrier fluid.

The boundary structures are arranged such that when a sufficiently large number of solid objects that cannot be deformed and have a circular cross section with a diameter equal to the spacing $a_0$ of the sensor array were placed on the first wall, the solid objects would arrange in a planar close-packing in which a respective solid object is aligned with each of the sensors. The solid objects may e.g. have a spherical, spheroidal, ellipsoidal or cylindrical shape. When projected along a direction perpendicular to the first wall, the close-packing of the solid objects may correspond to a close-packing of equal circles. A respective solid object may for example be placed above each of the sensors such that a center of the solid object in a plane parallel to the first wall is aligned with a center of the sensor and/or the solid object is arranged in the unit cell associated with the sensor, e.g. such that edges of the unit cell are tangential to a circumference of the solid object when viewed along a direction perpendicular to the first wall. As detailed above, the close-packing of the solid objects with the circular cross section may correspond to the densest possible arrangement of the solid objects under the boundary conditions imposed by the boundary structures in the measurement volume. In the resulting structure, each of the solid objects may be in contact with at least one other solid object. Furthermore, at least some of the solid objects may be in contact with one or more of the boundary structures. Contact between the solid objects and the boundary structures may break the intrinsic translational invariance of the uniform close-packing of equal circles and may thereby pin the solid objects to a desired arrangement. In some embodiments, one or more of the boundary structures may confine the solid objects by interactions mediated by a carrier fluid instead of or in addition to direct interactions with the solid objects. For example, a hydrophilic or hydrophobic coating may facilitate or prevent wetting of the respective surface by the carrier fluid, thereby confining objects provided in the carrier fluid. In other words, in some examples the close-packing of the solid objects in the measurement volume would only be formed and/or aligned with the sensor array if the solid objects were provided in a carrier fluid.

Accordingly, the two or more boundary structures may be configured to also confine a plurality of sample objects having a circular cross section, albeit not truly non-deformable solid objects as discussed above, to a self-organized close-packing of equal circles in the measurement volume such that a respective sample object is arranged adjacent to each of the sensors. In other words, when a sufficiently large number of sample objects is placed in the measurement volume, the sample objects form a self-organized structure in the measurement volume in which a respective sample object is aligned with each of the sensors in the sensor array. As detailed above for the method according to the invention, the same applies for sample objects that do not have a circular cross section, but are nonetheless configured to form a self-organized structure resembling a close-packing of equal circles. A physical dimension of the sample objects may for example be chosen such that the physical dimension of the sample objects corresponds to a spacing of the sensor array.

As detailed above, the sensor array may correspond to a tiling of identical unit cells with each sensor being associated with a respective unit cell. The boundary structures may for example be arranged such that segments of the boundary structures are aligned with edges of unit cells of the sensor array along the circumference of the sensor array, e.g. to confine the sample objects to respective unit cells in the self-organized structure by interactions between the sample objects and the boundary structures as well as by interactions between the sample objects themselves. Preferably, an edge of each of the outermost unit cells of the sensor array is aligned with one of the boundary structures.

In some embodiments, each of the outermost sensors in the sensor array may be arranged at a distance corresponding to one half of the first spacing $a_1$, i.e. a distance of $a_1/2$, from at least one of the boundary structures, wherein the distance between the sensor and a boundary structure may e.g. be the distance between a center of the sensor and the respective boundary structure. In this way, a sample object with a physical dimension corresponding to the first spacing, e.g. a diameter corresponding to the first spacing, that is aligned with one of the outermost sensors may be in contact with the respective boundary structure. The outermost sensors of the sensor array may for example be the sensors for which the respective solid object in the close-packing that is aligned with the sensor is not completely confined by the other solid objects in the close-packing, i.e. could be moved without moving another solid object if it were not for the boundary structures.

In some embodiments, the two or more boundary structures are arranged such that in the close-packing of the solid objects, in which a respective solid object is aligned with each of the sensors, e.g. aligned with the respective unit cell, contact between the solid objects and contact between the solid objects and the boundary structures prevent at least 90%, preferably at least 95% of the solid objects from moving in a plane parallel to the first wall.

In some embodiments, the two or more boundary structures comprise two opposing boundary structures that are separated by a distance D that is equal to an integer multiple of the spacing $a_0$ of the sensor array, i.e. $D=M\cdot a_0$ with M being a positive integer, in particular an integer greater than 1. The integer M may for example be between 5 and 1000, in one example between 10 and 100. This may for example allow for arranging M solid objects or sample objects with a physical dimension corresponding to $a_0$, e.g. a diameter corresponding to $a_0$, between the opposing boundary structures such that the M solid objects or sample objects are in contact with each other and the opposing boundary structures, thereby forming an approximately incompressible chain (e.g. a chain that can only be deformed by deforming the solid objects or sample objects).

Additionally or alternatively, the two or more boundary structures may comprise two opposing boundary structures that are separated by a distance D that is equal to $(1+\sqrt{3}\,N/2)$ times the spacing $a_0$ of the sensor array, i.e. $D=(1+\sqrt{3}N/2)\cdot a_0$, wherein N is a positive integer, in particular an integer greater than 1. The integer N may for example be between 4 and 999, in one example between 9 and 99. This may for example allow for arranging (N+1) linear chains of solid objects or sample objects having a circular cross section with a diameter corresponding to $a_0$ between the opposing boundary structures, wherein the solid objects or sample objects form a uniform close-packing of equal circles. Accordingly, the sample objects may be in contact with each other and the opposing boundary structures, thereby forming an approximately incompressible structure (e.g. a structure that can only be deformed by deforming the solid objects or sample objects).

As mentioned above, the sensor array may be a two-dimensional periodic array having a first spacing $a_1$ in a first direction and a second spacing $a_2$ in a second direction. The second spacing $a_2$ may be equal to the first spacing $a_1$ or may be different than the first spacing $a_1$. In some examples, the sensors in the array may e.g. be arranged in a rectangular lattice, wherein the second direction is perpendicular to the first direction and the second spacing is different from the first spacing.

In a preferred embodiment, the sensors in the array are arranged in a hexagonal lattice with a spacing $a_h=a_1=a_2$. A hexagonal lattice may be spanned by two primitive or translation vectors $\vec{\alpha}_1=(a_h, O)$ and $\vec{\alpha}_2=(a_h/2, \sqrt{3}\ a_h/2)$, corresponding to two sides of an equilateral triangle. The boundary structures may comprise a first pair of opposing boundary structures, in particular a first pair of opposing sidewalls of the measurement volume, and a second pair of opposing boundary structures, in particular a second pair of opposing sidewalls of the measurement volume. Preferably, each of the boundary structures or sidewalls extends parallel to a respective vector corresponding to a linear combination of the two primitive vectors, most preferably parallel or perpendicular to one of the primitive vectors. In some examples, the boundary structures or sidewalls of a given pair may be parallel to each other. The first pair of boundary structures or sidewalls may be separated by a first distance $D_1=(1+\sqrt{3}\ N_1/2)\cdot a_h$ with $N_1$ being a positive integer greater than 1. The second pair of boundary structures or sidewalls may be separated by a second distance $D_2$ with $D_2=(N_2+1)\cdot a_h$ or $D_2=(1+\sqrt{3}\ N_2/2)\cdot a_h$ with $N_2$ being a positive integer greater than 1. Each of the integers $N_1$ and $N_2$ may for example be between 4 and 999, in one example between 9 and 99. A distance between opposing boundary structures or sidewalls may for example be the smallest distance between the respective structures.

In some embodiments, the sensor chip may further comprise a droplet generator that is configured to generate microdroplets of a sample fluid in the carrier fluid, in particular monodisperse microdroplets, i.e. microdroplets with a uniform size. The droplet generator may for example be configured to generate the microdroplets by cross-flow droplet generation and may e.g. comprise a T-junction at which a first channel in which the carrier fluid is provided intersects under an angle with a second channel in which the sample fluid is provided. In other examples, the droplet generator may be configured to generate the microdroplets by co-flow droplet generation, by hydrodynamic flow focusing, and/or by step emulsification. A size of the microdroplets may for example be controlled by adjusting a flow velocity and/or a composition of the carrier and/or sample fluids.

In some embodiments, the sensor chip may comprise a microfluidic inlet channel and a microfluidic outlet channel, wherein the inlet and outlet channels are in fluid communication with the measurement volume. The sensor chip may further comprise means for selectively preventing the sample objects from leaving the measurement volume through the outlet channel. The sensor chip may for example comprise a valve that is configured to adjust a width or a cross-sectional area of a portion of the outlet channel, e.g. such that the carrier fluid can be released from the measurement volume through the outlet channel, but sample objects cannot pass through the valve.

Each of the sensing elements is configured to generate a sensor signal, in particular an optical, magnetic, and/or electrical sensor signal, wherein the sensor signal characterizes a physical observable in the vicinity of the respective sensing element, for example at the position of the respective sensing element or in a sensing volume around the respective sensing element, e.g. as detailed above for the method according to the invention. The sensor signal may for example characterize a temperature, a pH value, an electrical conductivity, a permittivity, an electric field, a magnetic field, and/or a light intensity. Each of the sensing elements may for example comprise one or more of an electrode, in particular an electrode that is exposed to the measurement volume, a capacitive sensing element, an inductive sensing element, a resistive sensing element, a piezoelectric sensing element, a Hall-effect sensing element and a photodiode.

In a preferred embodiment, the sensors are magnetic quantum sensors, wherein the sensing elements are magnetic quantum sensing elements and each of the sensors comprises a plurality of magnetic quantum sensing elements. The sensing elements may for example be optically addressable solid-state spin systems, e.g. as detailed above. The optically addressable solid-state spin systems may in particular be nitrogen-vacancy (NV) centers in diamond. NV centers may for example be used for locally measuring electric and magnetic fields, see e.g. R. Schirhagl et al., *Annu. Rev. Phys. Chem.* 65, 83-105 (2014), and for performing nuclear magnetic resonance (NMR) spectroscopy on small sample volumes, e.g. as reported in D. R. Glenn et al., *Nature* 555, 351-354 (2018) and WO 2018/052497 A2.

The solid-state spin systems may for example be arranged in sensing regions located in a sensing layer, which may e.g. be a surface layer underneath a surface of the first wall that is exposed to the measurement volume. The sensing layer may for example comprise or consist of diamond and may have a thickness perpendicular to the surface of between 1 μm and 1000 μm, in some examples between 2 μm and 100 μm, in one example between 5 μm and 10 μm. In some examples, the sensing layer may form the top surface of the first wall at least in part. In other examples, one or more additional layers may be arranged between the sensing layer and the surface of the first wall, e.g. an optical coating. In some examples, the spin systems may be confined to the sensing regions, whereas in other examples, the spin systems may be distributed over the entire surface layer. In some embodiments, a density of the spin systems in the sensing layer outside of the sensing regions may be at least a factor of 100, preferably at least a factor of 1000 smaller than a density of the spin systems within the sensing regions.

In some embodiments, the sensor chip may comprise a light guiding system that is configured to provide an optical path through the sensor chip, wherein the optical path connects some or all of the sensing regions, e.g. such that light propagating along the optical path sequentially passes through the respective sensing regions at least once. In other words, some or all of the sensing regions may be arranged along the optical path provided by the light guiding system. Preferably, light propagating along the optical path passes through each sensing region the same number of times, e.g. once.

The light guiding system may in particular comprise one or more optical elements that modify the propagation of light along the optical path such as a reflecting structure, an optical coating, and/or a waveguide. The light guiding system may for example comprise one or more reflective coatings, in particular a broadband or dichroic reflective coating. The reflective coatings may for example be arranged on the surface of the first wall exposed to the measurement volume, on a bottom surface of the substrate opposing the surface of the first wall and/or on one or more side faces of the substrate extending between the top and bottom surfaces. In some examples, the propagation of light along the optical path may also comprise one or more total internal reflections at a surface of the sensor chip, i.e. the light guiding system may be configured such that an angle of incidence of the optical path on the respective surface is larger than the critical angle for total internal reflection.

In some embodiments, at least two segments of the optical path are not parallel to each other, e.g. due to a reflection off a reflecting element of the light guiding system or due to a curved or bend portion of a waveguiding element of the light guiding system. Each of the nonparallel segments may in particular be arranged or extend between two or more of the sensing regions. In some examples, the optical path may additionally comprise one or more sets of parallel segments. The optical path may for example form a periodic pattern, e.g. a zig-zag pattern and/or a meandering pattern, in one or more planes, e.g. in a plane perpendicular or parallel to a surface of the first wall. In some examples, the optical path may form a non-intersecting pattern, in particular a non-intersecting periodic pattern.

The sensors and/or the sensing elements may be exposed to the measurement volume or may be separated from the measurement volume by a portion of the first wall. The sensors and/or the sensing elements may for example be fully embedded in the first wall or may be arranged in a layer underneath the first wall. A distance between each of the sensors and the surface of the first wall exposed to the measurement volume may for example be less than five times, preferably less than two times the spacing $a_0$ of the sensor array. In some examples, the distance between the sensors and the surface of the first wall may be equal to or smaller than the spacing $a_0$, in one example less than 50% of the spacing $a_0$. This may facilitate interaction between the respective sensing elements and a sample object in the measurement volume and may reduce cross-talk between the sensors. The distance between a sensor and the surface of the first wall may for example be the distance between a center of the sensor and the surface of the first wall.

The invention further provides a sensing device for parallelized probing of a plurality of samples using a method according to any one of the embodiments described herein. The sensing device comprises a sensor chip, wherein the sensor chip comprises a substrate and a measurement volume configured to receive a carrier fluid comprising a plurality of sample objects. The substrate comprises a plurality of optically addressable sensing elements arranged in a sensing layer in or below a first wall of the measurement volume, wherein each of the sensing elements is configured to generate a sensor signal characterizing a physical observable in the vicinity of the respective sensing element. The sensing device further comprises an illumination system for illuminating the sensing elements. The sensor chip comprises two or more boundary or guiding structures configured to confine or guide a motion of the sample objects in the measurement volume. The two or more boundary or guiding structures are arranged such that when solid objects having a circular cross section with a diameter d are placed in the measurement volume with the solid objects covering the entire first wall of the measurement volume, the solid objects arrange in a self-organized structure in which a plurality of subsets of the solid objects are each arranged along a respective one of a plurality of straight lines. The illumination system is configured to provide a plurality of illumination light beams, each of which propagates through the substrate along an optical path aligned with a respective one of the plurality of straight lines for illuminating sensing elements adjacent to the solid objects of the respective subset in the self-organized structure.

The sensing device according to the invention provides an alternative way of implementing the method according to the invention as compared to the sensor chip according to the invention. While the sensor chip according to the invention provides boundary structures that allow for arranging a plurality of sample objects in a self-organized structure that is adapted to an array of individual, spatially separated sensors on the sensor chip as detailed above, the sensing device according to the invention provides means for selectively illuminating sensing elements, which may e.g. be distributed homogeneously throughout the sensing layer, using a pattern of light that is adapted to a self-organized structure of the sample objects in the measurement volume as imposed by the boundary structures. In this way, sensing regions adjacent to the sample objects in the self-organized structure may for example be activated and/or read out selectively, thereby forming an "illumination-induced" array of sensors adapted to the self-organized structure.

The sensor chip of the sensing device may be similar at least in part to any one of the embodiments of the sensor chip according to the invention described herein. For example, the substrate, the measurement volume, and/or the boundary structures of the sensor chip of the sensing device may be similar to the respective elements described above and description thereof is omitted here for the sake of brevity. The sensor chip may also comprise additional components as described above for the sensor chip according to the invention, for example a droplet generator, microfluidic inlet and/or outlet channels, and/or a valve. In some embodiments, the sensor chip of the sensing device may be a sensor chip according to one of the embodiment of the invention described herein. The sensing elements in the sensing layer may for example form an array of spatially separated sensing regions or sensors.

The sensing layer, in which the optically addressable sensing elements are arranged, may form at least a part of the first wall, i.e. may have a surface that is exposed to the measurement volume. The sensing layer may for example be a surface layer of the substrate or may be arranged or deposited on a surface layer of the substrate. In other embodiments, one or more layers, e.g. an optical coating and/or a hydrophilic or hydrophobic coating, may be arranged between the sensing layer and the measurement volume such that the sensing layer is not exposed to the first volume.

In the context of this disclosure, an optically addressable sensing element refers to a sensing element whose state can be changed using light. The sensing elements may for example be configured to be activated optically. Each of the sensing elements may e.g. be configured to be switched from an off-state, in which the sensing element does not generate a sensor signal, to an on-state, in which the sensing element generates a sensor signal, using light. Additionally or alternatively, the sensing elements may for example be configured to be read out optically. Each of the sensing elements may e.g. be configured to be excited optically from a first state to a second state and to generate the sensor signal in response to the excitation. The sensor signal may in particular be an optical sensor signal. The sensor signal may for example be an intensity of light emitted by the respective sensing element following the optical excitation, e.g. a fluorescence intensity, or an intensity of light absorbed by the respective sensing element due to the optical excitation.

In a preferred embodiment, the sensing elements are optically addressable solid-state spin systems, e.g. nitrogen-vacancy centers.

The boundary structures are arranged such that the solid objects in the self-organized structure form a plurality of subsets, wherein solid objects of a given subset are arranged along a respective straight line. As detailed above, this may also allow for arranging sample objects in a corresponding self-organized pattern, in particular sample objects having a circular cross section with the same diameter d. The solid objects of a given subset may for example form a linear chain with each of the solid objects being in contact or close proximity to two adjacent solid objects. Each of the subsets may for example comprise between 5 and 1000 solid objects, in some examples between 10 and 100 solid objects. The self-organized structure may e.g. comprise between 2 and 100, in some examples between 5 and 20 of such subsets. Some or preferably all of the straight lines may be parallel to each other, i.e. the respective subsets may be arranged in parallel. In some embodiments, the self-organized structure may be a uniform close-packing of equal circles or spheres and the plurality of straight lines may be parallel to a primitive vector of the corresponding hexagonal lattice. Each of the solid objects in the self-organized structure may be part of a subset in some examples, whereas in other examples, one or more solid objects in the self-organized structure may not be part of a subset.

The illumination system may comprise one or more optical elements such as beam splitters, diffractive optical elements, reflective coatings, mirrors, wave guides, and/or lenses to provide the plurality of illumination light beams. The illumination system is configured to provide the illumination light beams such that each of the illumination light beams propagates through the substrate along an optical path that is aligned with a respective straight line and thus with the respective subset of solid objects in the self-organized structure. The optical path may for example extend such that the optical path can be projected onto the respective straight line along a direction perpendicular to the straight line, i.e. overlaps with the straight line when viewed along the direction perpendicular to the straight line. In other words, the optical path may extend in a plane containing the straight line and may in particular be parallel to the straight line. At least a part of the optical paths extends through the sensing layer such that sensing elements can be illuminated by the illumination light beams. Light for generating the illumination light beams may be provided by one or more external light sources such as a laser. The illumination system may not comprise any light sources in some embodiments. In other embodiments, the illumination system may also comprise one or more light sources for generating the illumination light beams.

The illumination system may be configured to split an incoming light beam into the plurality of illumination light beams. The incoming light beam may e.g. be provided by an external light source or a light source forming part of the illumination system. The illumination system may for example comprise one or more beam splitters, wherein each of the beams splitter may e.g. be configured to split an illumination light beam from the incoming light beam and to couple the illumination light beam into the respective optical path. The beams splitters may for example be non-polarizing beam splitters, which may be configured to split the incoming light beam by means of a partially reflective surface or interface, and/or polarizing beam splitters, which may be configured to split the incoming light beam by means of a surface of interface having a polarization dependent reflectivity. Additionally or alternatively, the illumination light system may also comprise one or more diffractive optical elements, each of which is configured to split a light beam such as the incoming light beam into two or more beams by means of diffraction.

Some or all of the optical paths of the illumination light beams may be parallel to each other, wherein the optical paths may for example be arranged at a uniform spacing $A_1$ between adjacent optical paths. The optical paths may in particular be separated by a spacing $A_1=d$ or $A_1=\sqrt{3}/2\cdot d$, i.e. by a spacing corresponding to the diameter of the solid objects ($A_1=d$) and a spacing corresponding to the distance between adjacent linear chains of solid objects in a uniform close-packing of equal circles or spheres ($A_1=\sqrt{3}/2$ d).

One or more of the optical paths of the illumination light beams, in some examples all of the optical paths of the illumination light beam may extend through the sensing layer at an angle of less than 10°, preferably less than 5° to the first wall of the measurement volume. In some embodiments, each of the respective optical paths may comprise a reflection at a surface above or below the sensing layer, e.g. a total internal reflection at the first wall of the measurement volume or a reflection at a reflective coating on the first wall. In other embodiments, the respective optical paths may be parallel to the first wall of the measurement volume.

Additionally or alternatively, for one or more of the optical paths of the illumination light beams, in some examples for all of the optical paths of the illumination light beams, light propagating along the respective optical path may be sequentially reflected off a first surface above the sensing layer and a second surface below the sensing layer such that the optical path intersects with the sensing layer in sensing regions. The sensing regions may correspond to the portions of the sensing layer in which sensing elements are illuminated by the illumination light beams and thus can be addressed optically using the illumination system, e.g. to activate and/or read-out the respective sensing elements. The optical path of an illumination light beam sequentially passes through each of the corresponding sensing regions such that the sensing elements in these sensing regions may be addressed using a single beam of light. Preferably, each of the sensing regions is adjacent to a respective one of the solid objects in the self-organized structure, e.g. such that a center of the sensing region is aligned with a center of the respective solid objects in the self-organized structure. This may e.g. allow for a targeted addressing of sensing elements in the vicinity of sample objects in a corresponding self-organized structure.

The reflection at the first surface and/or at the second surface may for example occur by total internal reflection at the respective surface or interface. In some embodiments, the illumination system may also comprise a reflective coating on the first surface and/or on the second surface, wherein the reflective coating is configured to reflect the illumination light beams. The first surface may be in close proximity to the sensing layer and may e.g. be less than 2 μm, in some examples less than 1 μm from a top surface of the sensing layer. The distance between the top surface of the sensing layer and the first surface may be chosen such that portions of the respective optical path in the sensing layer prior to and after the reflection at the first surface are sufficiently close to each other such that a single sensing region is formed, e.g. such that a distance between the respective portions is smaller than a diameter of the illumination light beam. The first surface may for example be the first wall of the measurement volume and/or may be the top surface of the sensing layer. The second surface may be arranged at a larger distance from the sensing layer, e.g. at a distance between 10 μm and 1000 μm from a bottom surface of the sensing layer, such that a portion of the respective optical path prior to and after the reflection at the second surface is arranged outside of the sensing layer, thereby allowing for forming spatially separated sensing regions. The second surface may for example be a bottom surface of the substrate. Preferably, the first and second surfaces are parallel to each other.

In some embodiments, the sensing elements may be distributed homogeneously throughout the sensing layer, e.g. such that a density of the sensing elements or a mean spacing between adjacent sensing elements is uniform within the sensing layer. Accordingly, sensing elements may not only be arranged in the vicinity of the optical paths of the illumination light beams, but may also be arranged in other portions of the sensing layer. The illumination light beams propagating through the substrate may define sensing regions, i.e. portions of the sensing layer in which sensing elements are illuminated and can thus be addressed by the illumination light beams, e.g. for selective activation and/or read-out of the respective sensing elements. As a result of the alignment between the optical paths of the illumination light beams and the solid objects in the self-organized structures, these "illumination-induced" sensing regions also form a pattern that is adapted to the self-organized structure. The sensing regions may for example be strip-like portions or regions of the sensing layer extending parallel to a subset of solid objects in the self-organized structure or may form an array of spatially separated sensing regions, which may match the arrangement of the solid objects in the self-organized structure.

In other embodiments, the sensing elements may not be distributed throughout the sensing layer, but may be confined to portions of the sensing layer. The sensing elements may for example be confined to an array of spatially separated sensing regions as detailed above for the sensor chip according to the invention.

In some embodiments, each of the sensing elements may be configured to generate an optical sensor signal, wherein the optical sensor signal may for example be light emitted or transmitted by the respective sensing element. The sensing device may further comprise a photosensitive detector that is configured to record the sensor signals of the sensing elements, e.g. by determining an intensity of the light emitted or transmitted by one or more of the sensing elements. The photosensitive detector may in particular be configured to record a spatially resolved image of the sensor signals of the sensing elements, i.e. to record the sensor signals of the sensing elements as a function of position within the sensing layer. The photosensitive detector may for example be configured to determine an intensity of light as a function of position within the sensing layer, e.g. in a plane parallel to the first wall of the measurement volume. The photosensitive detector may for example comprise a camera chip with a plurality of photosensitive pixels such as a CCD or CMOS chip, onto which the sensing layer or a portion thereof is imaged, e.g. using a microscopic imaging system.

The sensing device may comprise a controller that is configured to obtain the spatially resolved image of the sensor signals from the photosensitive detector. The controller may be implemented in hardware, software or a combination thereof. The controller may for example comprise a processor and a memory storing instructions for execution by the processor to provide the functionality described herein. The controller may be configured to select, for each of at least some of the solid objects in the self-organized structure, a region-of-interest in the spatially resolved image, wherein the region-of-interest contains sensor signals originating from a sensing region adjacent to the respective solid object in the self-organized structure. Thereby, the controller may also be configured to selectively determine sensor signals associated with a certain sample object in a corresponding self-organized structure, e.g. as detailed above for the method according to the invention. The region-of-interest may for example correspond to a portion of the photosensitive detector onto which the respective sensing region is imaged. In other examples, the region-of-interest may be smaller than the sensing region and may e.g. only contain sensor signals originating from a center portion of the respective sensing region. The region-of-interest may for example be a region of predetermined size around a point in the spatially resolved image that is associated with a center of the respective solid object or sample object. The controller may store a list of positions associated with the solid objects in the self-organized structure for selecting the region-of-interests. In other examples, the controller may be configured to determine a position of the respective solid objects or sample objects in the measurement volume, e.g. from an image of the respective objects in the measurement volume, and to select the regions-of-interest accordingly.

In a preferred embodiment, the sensing elements are optically addressable solid-state spin systems, in particular diamond color centers, for example nitrogen-vacancy centers in diamond. As detailed above, the solid-state spin systems may be distributed homogeneously throughout the sensing layer or may be confined to spatially separated sensing regions within the sensing layer. In some examples, a density of the solid-state spin systems in the substrate outside of the sensing regions may e.g. be at least a factor of 100, preferably at least a factor of 1000 smaller than a density of the solid-state spin systems within the sensing regions.

The sensing device may further comprise a mount that is configured to receive the sensor chip, e.g. to hold the sensor chip at a fixed position relative to the illumination system. In some embodiments, the illumination system or a part thereof is arranged on the mount, e.g. on a frame of the mount in which the sensor chip is to be placed. The mount may be adjustable and may e.g. be configured to move and/or tilt the sensor chip and/or the illumination system, for example to align the sensor chip and/or the illumination system relative to each other and/or relative to an incoming light beam provided by a light source.

The invention further provides a measurement system for parallelized probing of a plurality of samples using a method according to any one of the embodiments described herein. The measurement system comprises a mount that is configured to receive a sensor chip, wherein the sensor chip comprises a sensing layer arranged in or on a substrate and a measurement volume adjacent to the sensing layer. The sensing layer comprises a plurality of sensing elements, each of which is configured to generate a sensor signal characterizing a physical observable in the vicinity of the respective sensing element. The measurement system further comprises a microfluidics unit configured to provide a carrier fluid comprising a plurality of sample objects to the measurement volume when the sensor chip is arranged in the mount. The measurement system also comprises a measurement device that is configured to read out sensor signals from the sensing elements when the sensor chip is arranged in the mount. The measurement system further comprises a controller, wherein the controller is configured to control the microfluidics unit and the measurement device. The controller is configured to control the microfluidics unit to control a number of sample objects in the measurement volume such that the sample objects form a self-organized structure in the measurement volume. The controller is further configured to control the measurement device to perform a measurement on one or more of the samples while the sample objects are arranged in the self-organized structure, wherein a measurement on a sample is performed using one or more sensing elements arranged adjacent to the respective sample object in the self-organized structure.

The measurement system may in particular be configured for use with a sensor chip and/or a sensing device according to one of the embodiments described herein. In some examples, the measurement system may also comprise one or more sensor chips according to one of the embodiments described herein, an illumination system for providing a plurality of illumination light beams as described above, and/or a sensing device according to one of the embodiments described herein.

The microfluidics unit may comprise one or more reservoirs, e.g. for the carrier fluid and/or the sample fluid, as well as one or more connectors that are configured to be connected to an input or output port of the sensor chip for providing or removing the carrier fluid and/or the sample fluid. The microfluidics unit may further comprise one or more pumps for generating a flow of the carrier fluid and/or of the sample fluid. In some embodiments, the microfluidics unit may also comprise a droplet generator for preparing the sample objects in the carrier fluid, e.g. as described above. In other examples, the microfluidics unit may be configured to supply the carrier fluid and the sample fluid to the sensor chip separately, e.g. to a droplet generator on the sensor chip, or the sample objects may be prepared in the carrier fluid prior to providing the carrier fluid to the microfluidics unit.

The measurement device may for example comprise a plurality of measurement channels, wherein each measurement channel may e.g. be associated with a respective sensor or sensing region on the sensor chip and configured to read out a sensor signal from the respective sensor or sensing region. As detailed above, the sensor signal may for example be an electrical or optical signal. Accordingly, each measurement channel may for example comprise a voltmeter, an ammeter and/or a photosensitive detector, e.g. a photodiode or photomultiplier. The measurement device may in particular comprise a photosensitive detector configured to record a spatially resolved image of optical sensor signals of the sensing elements as described above for the sensing device according to the invention.

The controller may be implemented in hardware, software or a combination thereof. The controller may for example comprise a processor and a memory storing instructions for execution by the processor to provide the functionality described herein. The controller may for example be configured to generate a control signal for a pump or a valve of the microfluidics unit to control the number of sample objects in the measurement volume. The controller may further be configured to determine the number of sample objects in the measurement volume, e.g. by monitoring a flow rate of the carrier fluid and/or of the sample fluid, using an optical or electromagnetic droplet detector, and/or using a camera. The controller may in particular be configured to track sample objects on the sensor chip. The controller may further be configured to generate a control or trigger signal for the measurement device to initiate the measurement on the one or more samples once the self-organized structure is formed. The controller may also be configured to read out a measurement result from the measurement device, wherein the measurement result may e.g. be an analog or digital signal quantifying the sensor signal. In some embodiments, the controller may further be configured to execute some or all of the steps of a method for parallelized probing of a plurality of samples according to any one of the embodiments disclosed herein. The controller may also be configured to provide some or all of the functionality of the controller of the sensing device according to the invention described above, i.e. the controller of the sensing device may be integrated into the controller of the measurement system at least in part.

The invention further provides a set comprising a measurement system according to any one of the embodiments described herein and a sensor chip according to any one of the embodiments described herein, wherein the measurement system is adapted for use with the respective sensor chip. In particular, the mount of the measurement system may be configured to receive the respective sensor chip. Furthermore, the microfluidics unit may be configured to provide the carrier fluid comprising the plurality of sample objects to the measurement volume of the sensor chip and the measurement device may be configured to read out a sensor signal from each of the sensors in the sensor array of the sensor chip.

The invention also provides a set comprising a measurement system according to any one of the embodiments described herein and a sensing device according to any one of the embodiments described herein, wherein the measurement system is adapted for use with the respective sensor chip. In particular, the mount of the measurement system may be configured to receive the sensor chip of the sensing device. The illumination system of the sensing device and the measurement system or a part thereof may be provided as a single integrated system. For example, the illumination system or a part thereof may be arranged on the mount of the measurement system. The microfluidics unit may be configured to provide the carrier fluid comprising the plurality of sample objects to the measurement volume of the sensor chip and the measurement device may be configured to read out sensor signals from the sensing elements on the sensor chip, e.g. as described above.

LIST OF FIGURES

Figure 1B:
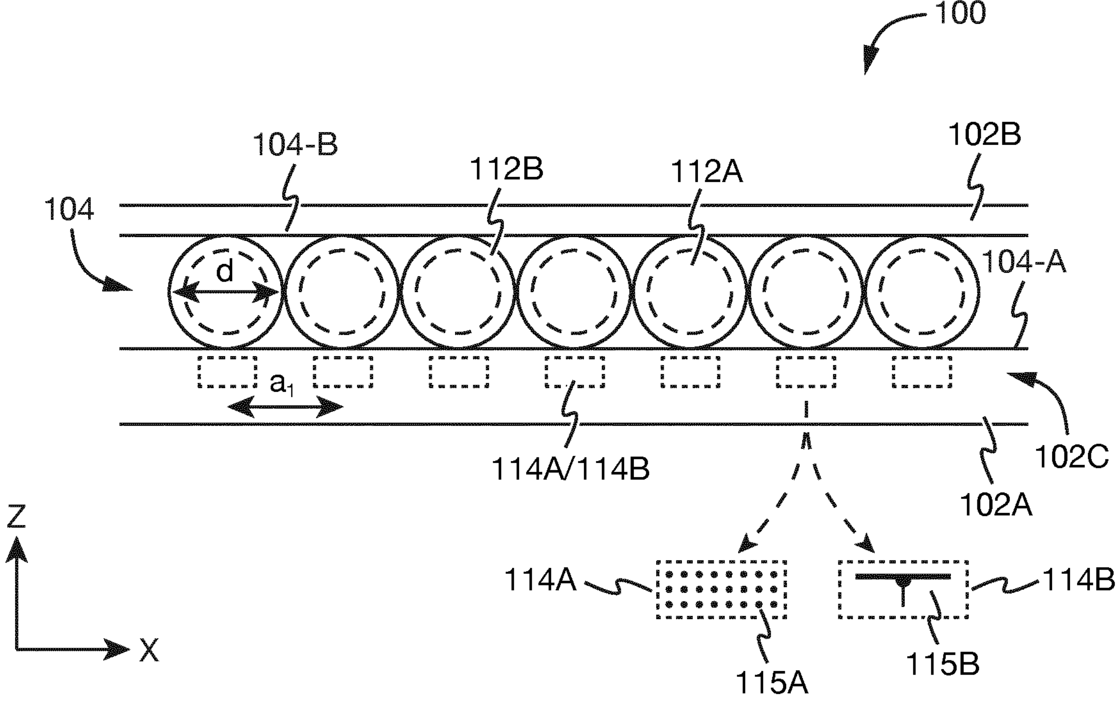
Figure 2:
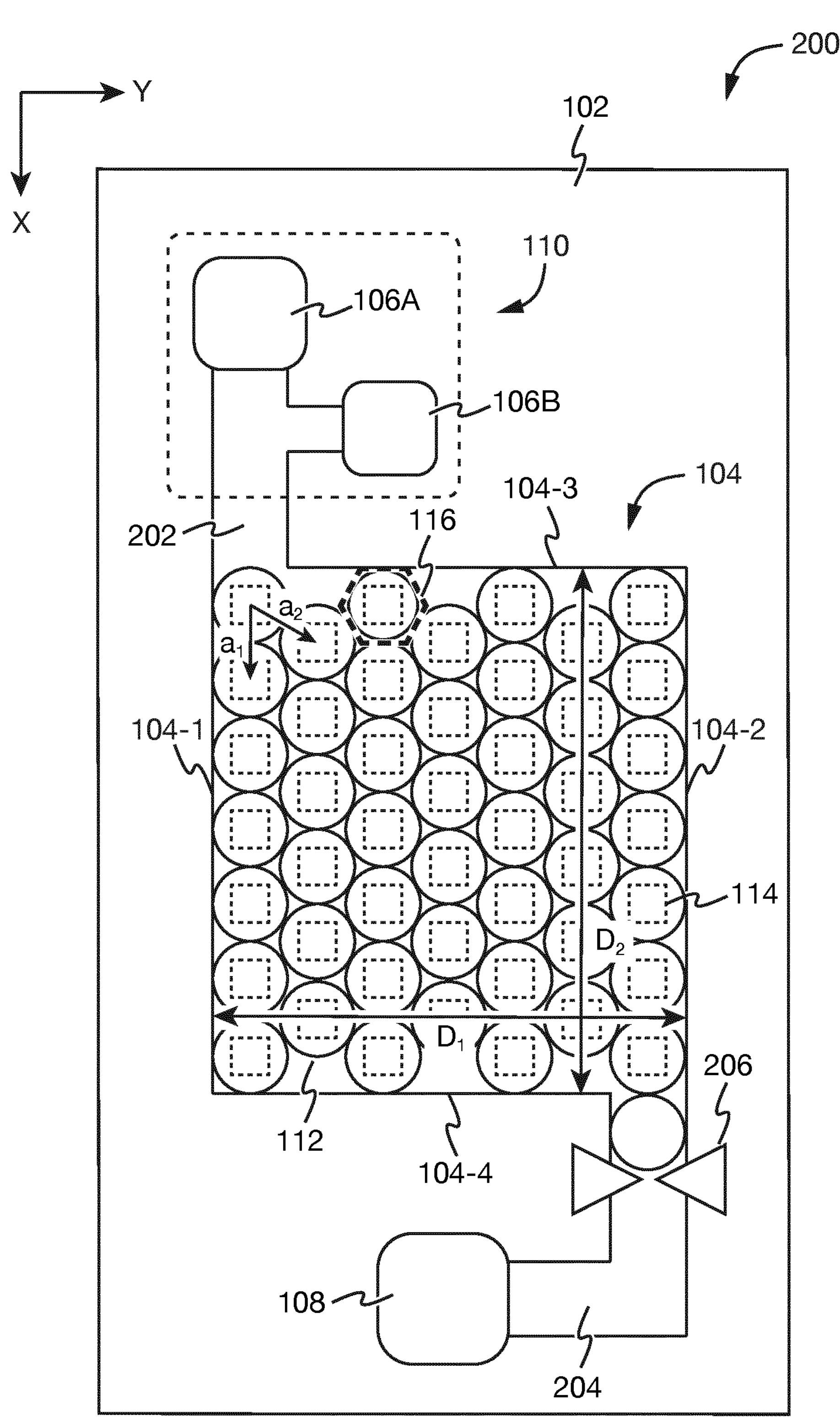
Figure 3A:
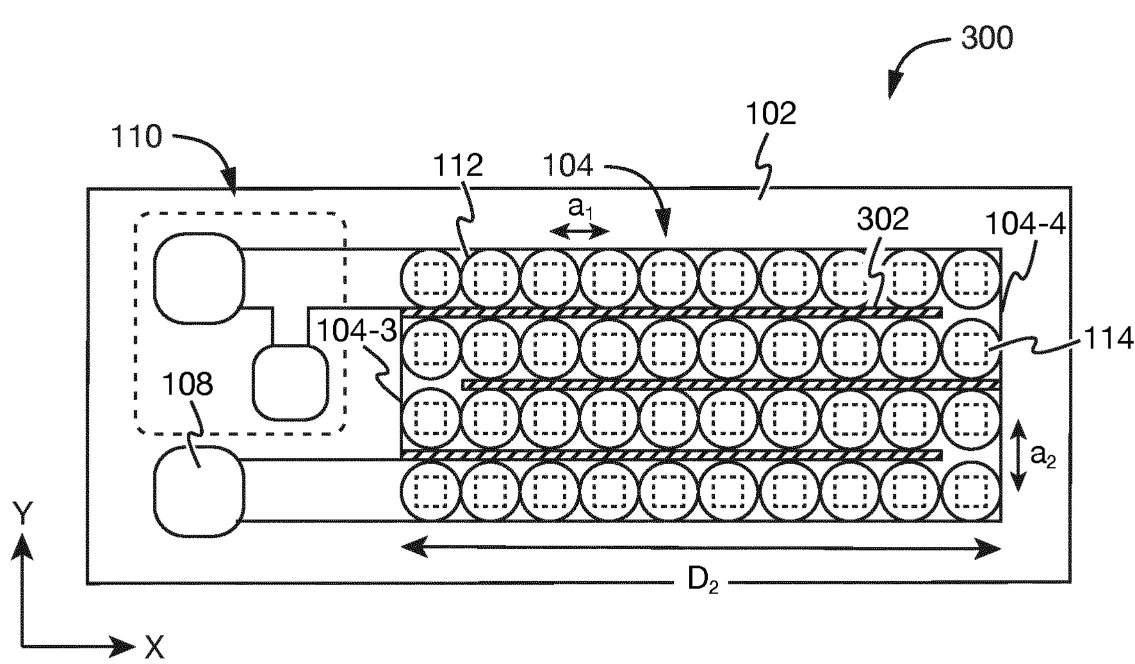
Figure 3B:
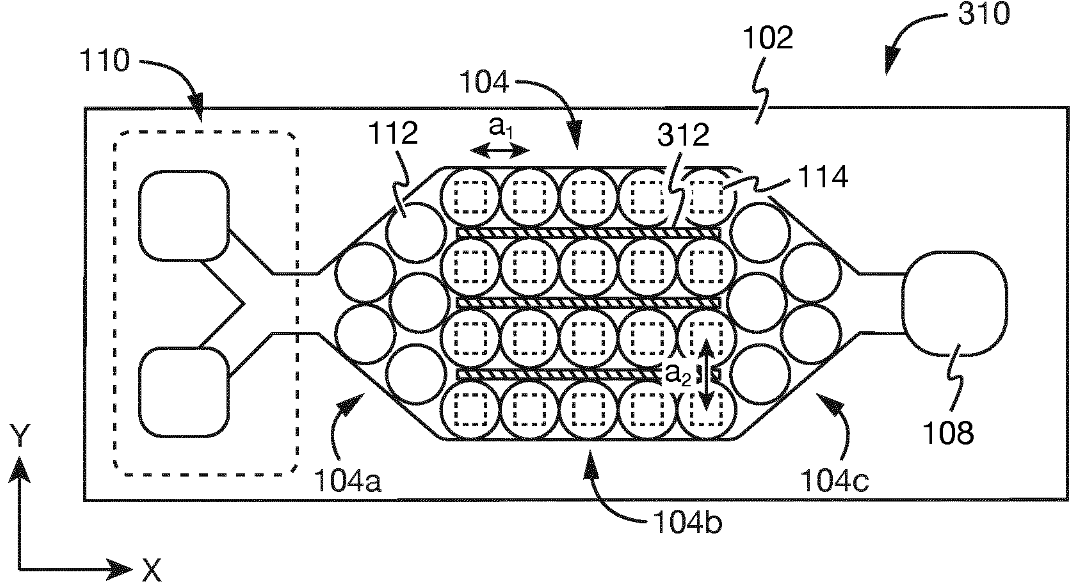
Figure 4:
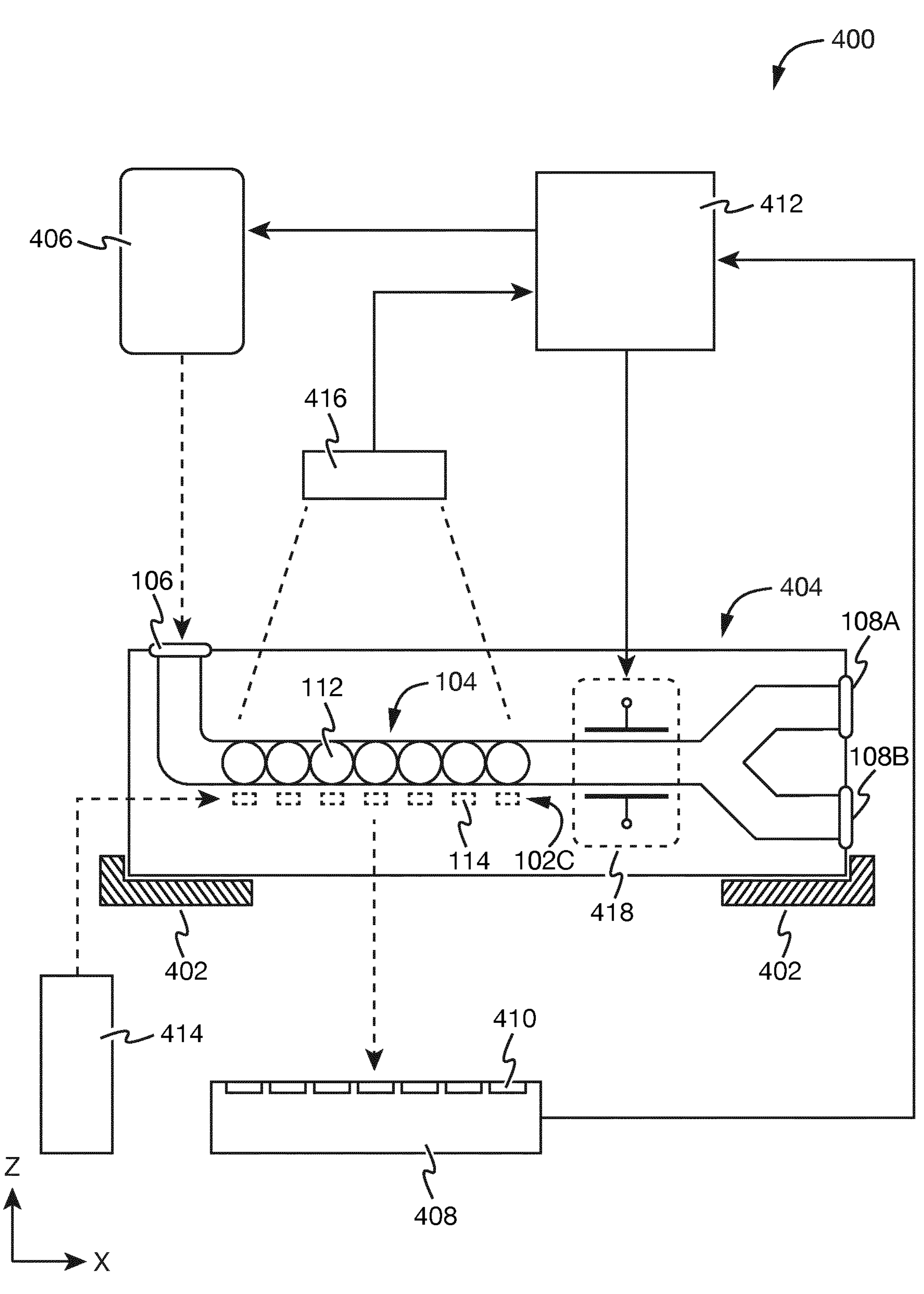
Figure 5:
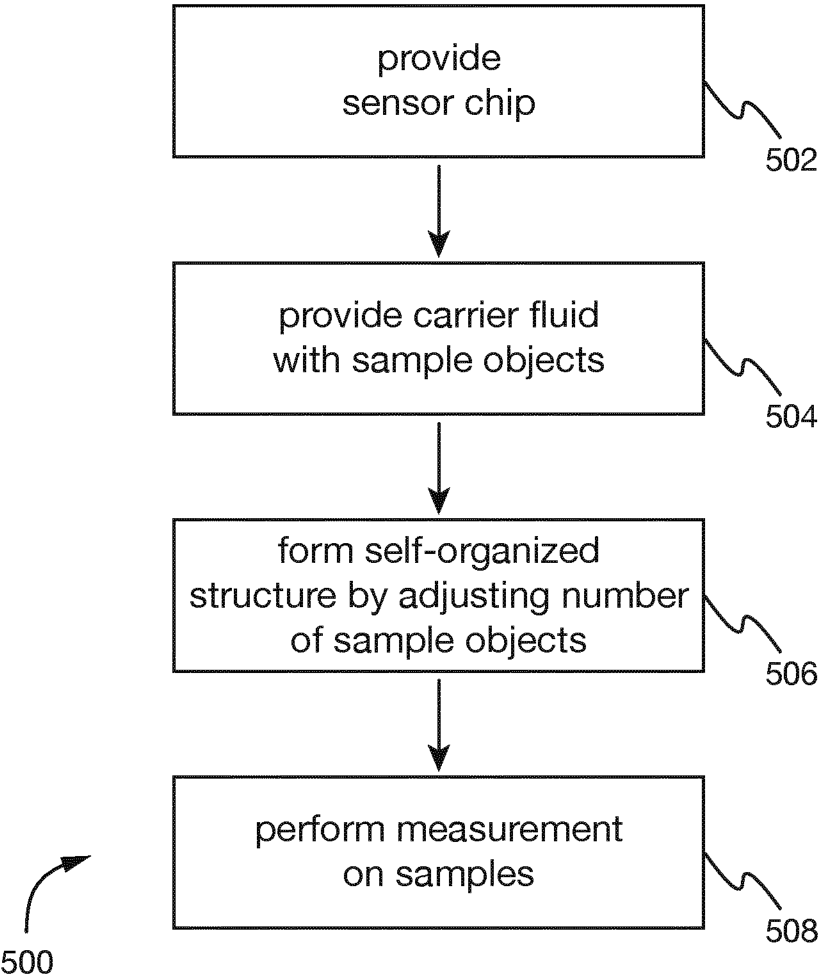
Figure 6:
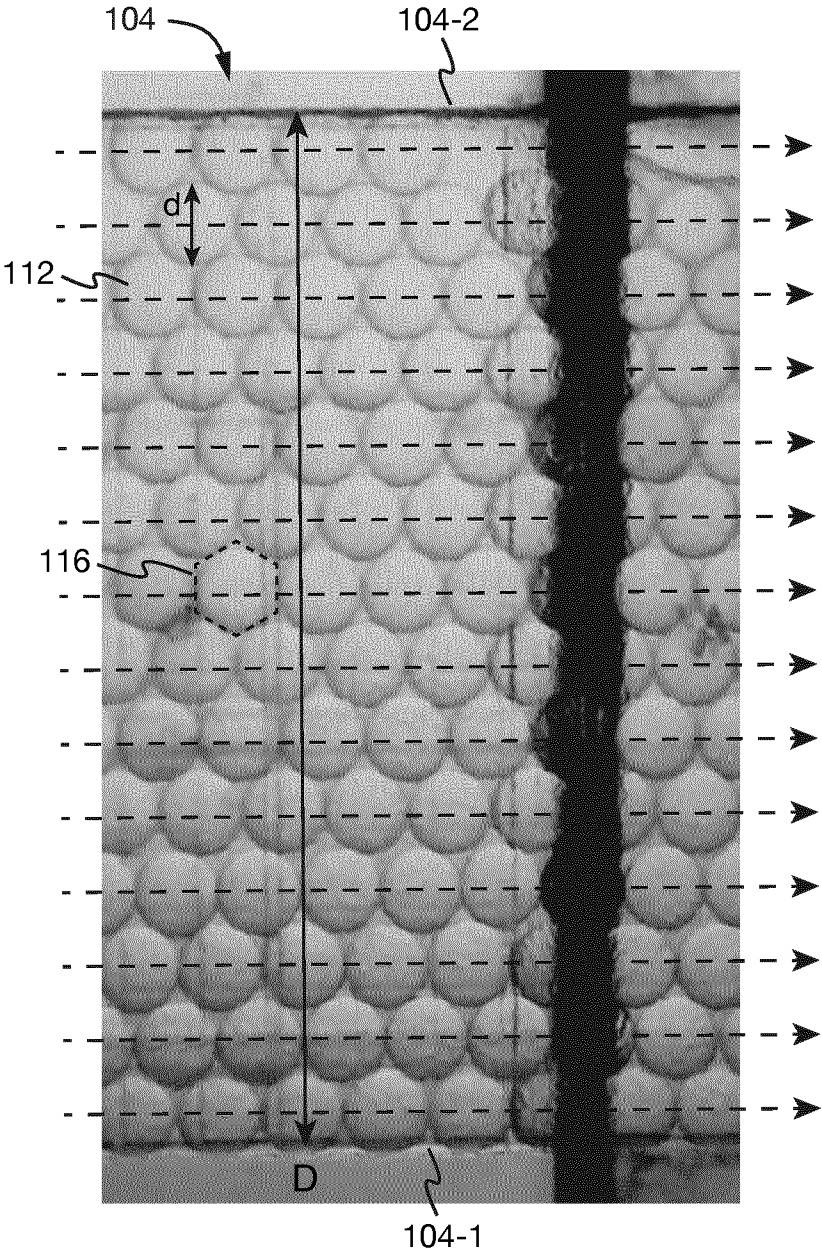
Figures 7A, 7B:
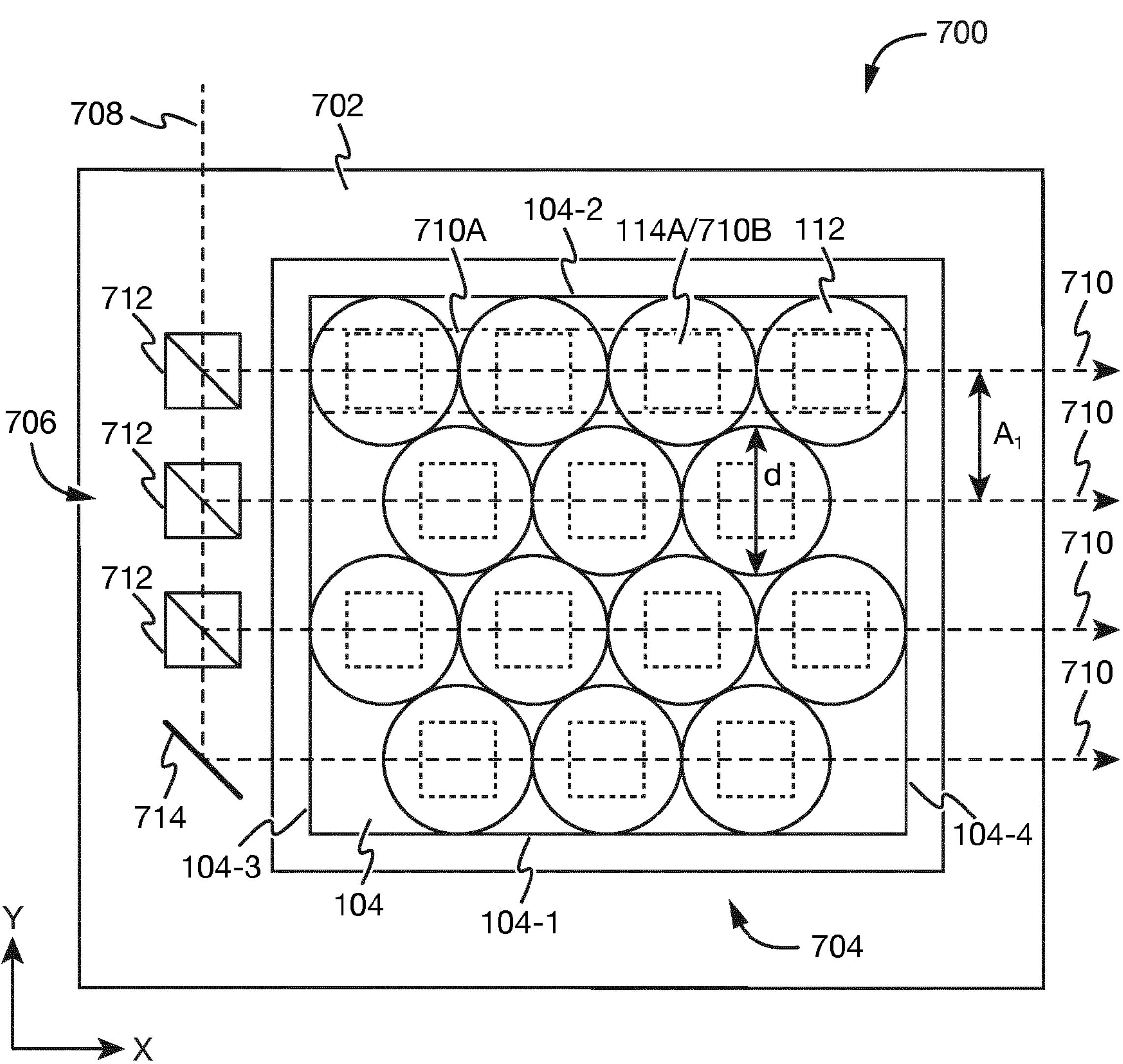
Figure 8:
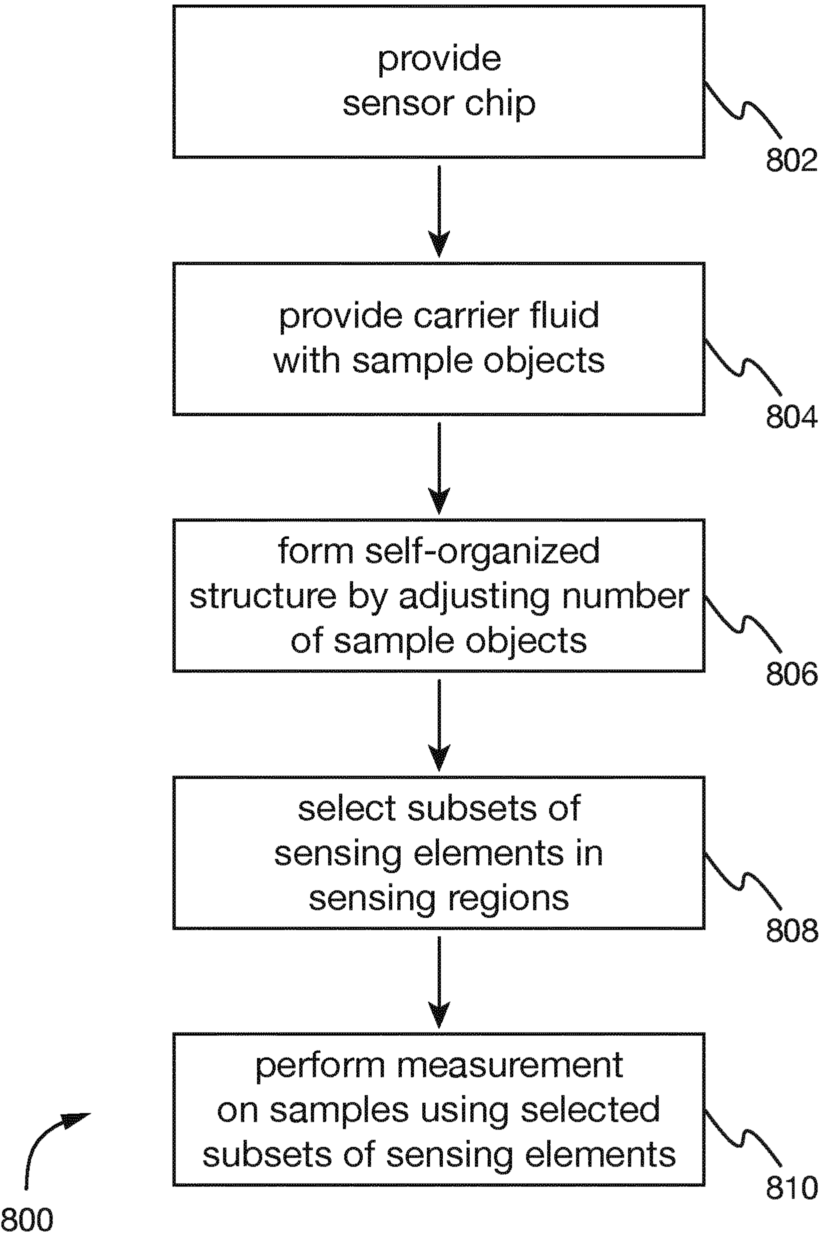
Figure 9:
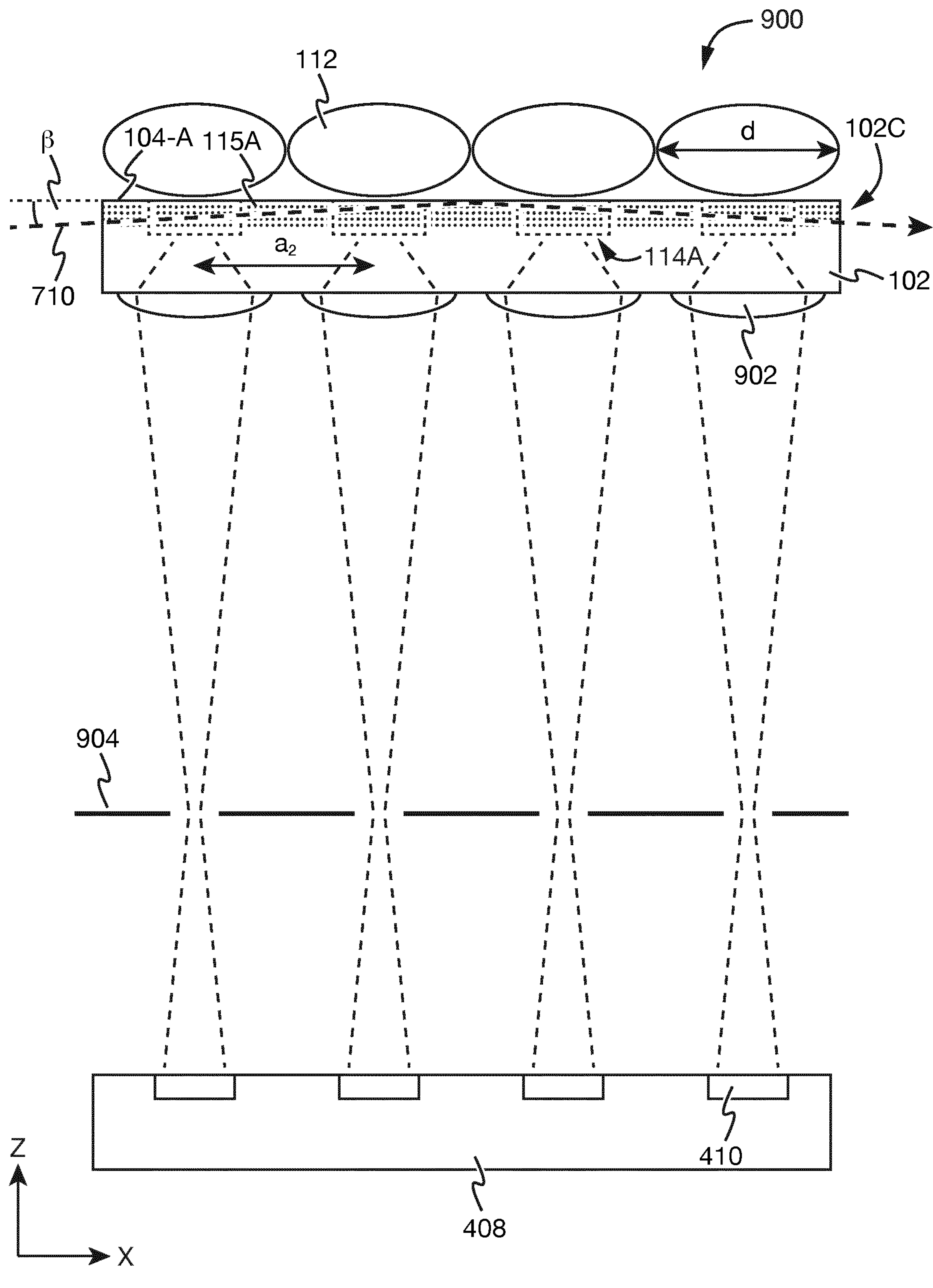

In the following, a detailed description of the invention and exemplary embodiments thereof is given with reference to the figures. The figures show schematic illustrations of FIG. 1*a*: a sensor chip according to an exemplary embodiment of the present invention in top view;

FIG. 1*b*: the sensor chip of FIG. 1*a* in side view;

FIG. 2: a sensor chip with a hexagonal sensor array in accordance with an exemplary embodiment of the invention in top view;

FIG. 3*a*: a sensor chip comprising guiding walls according to an exemplary embodiment of the invention in top view;

FIG. 3*b*: a sensor chip comprising hydrophilic or hydrophobic coatings in accordance with an exemplary embodiment of the invention in top view;

FIG. 4: a measurement system according to an exemplary embodiment of the invention in side view;

FIG. 5: a flow diagram of a method for parallelized probing of a plurality of samples in accordance with an exemplary embodiment of the invention;

FIG. 6: a microscopic image of a plurality of microdroplets arranged in a self-organized periodic structure on a sensor chip according to an exemplary embodiment of the invention;

FIG. 7*a*: a sensing device according to an exemplary embodiment of the present invention in top view;

FIG. 7*b*: a sensor chip of the sensing device of FIG. 7*a* in side view;

FIG. 8: a flow diagram of a method for parallelized probing of a plurality of samples comprising a selection of subsets of sensing elements in accordance with an exemplary embodiment of the invention; and FIG. 9: a sensor chip of the sensing device of FIG. 7*a* in accordance with another exemplary embodiment of the invention.

DESCRIPTION OF THE PREFERRED EMBODIMENTS

FIGS. 1*a* and 1*b* depict a schematic illustration (not to scale) of a sensor chip 100 for parallelized probing of a plurality of samples 112A according to an exemplary embodiment of the invention. The sensor chip 100 is shown in top view in FIGS. 1*a* and 1*n* side view in FIG. 1*b*.

The sensor chip 100 comprises a substrate 102, which may be a single-layer or multilayer substrate and may for example comprise or consist of an optically transparent material such as glass and/or a transparent thermoplastic such as poly(methyl methacrylate) (PMMA). Preferably, the substrate 102 comprises or consists of diamond. The substrate 102 may in particular comprise one or more layers or portions that consist of diamond, e.g. at least a sensing layer 102C. In the example of FIG. 1*a*, 1*b*, the substrate 102 comprises a lower substrate 102A and an upper substrate or cover 102B, which may be removably placed on the lower substrate 102A, e.g. to open or close a measurement volume 104 of the sensor chip 100. In other examples, the lower and upper substrates 102 may be permanently attached to each other or may be formed as a single piece. In yet another example, the sensor chip 100 may not comprise the cover 102B. A thickness of the lower substrate 102A perpendicular to a top surface of the lower substrate 102A, i.e. parallel to the Z axis of FIG. 1*b*, may for example be between 10 m and 5 mm. A cross-sectional area of the sensor chip 100 in the XY plane of FIG. 1*a*, which may also be referred to as the horizontal plane in the following, may for example be between 0.01 $mm^2$ and 100 $cm^2$, in some examples between 0.1 $cm^2$ and 10 $cm^2$.

The sensor chip 100 comprises a measurement volume 104, which in the example of FIG. 1*a*, 1*b* is formed by a recess in the top surface of the lower substrate 102A, which may be covered by the cover 102B to seal off the measurement volume 104. Accordingly, the bottom surface of the recess forms a first or bottom wall 104-A of the measurement volume 104 and a bottom surface of the cover 102B forms a second or top wall 104-B of the measurement volume 104 that opposes the bottom wall 104-A. The measurement volume 104 may for example have a height between 10 m and 1 mm, wherein the height of the measurement volume 104 is the distance between the bottom wall 104-A and the top wall 104-B. In the example of FIGS. 1*a*, 1*b*, the measurement volume 104 is a microfluidic channel extending along the X direction, wherein a width D of the measurement volume 104 perpendicular to a direction of flow in the microfluidic channel may for example be between 10 m and 100 m and a length of the measurement volume 104 parallel to the direction of flow may for example be between 100 m and 10 mm.

The sensor chip 100 further comprises two inlets or input ports 106A, 106B and an outlet or output port 108, which are in fluid communication with the measurement volume 104 and may for example be used to supply or remove fluids to/from the measurement volume 104. The sensor chip 100 also comprises a droplet generator 11*o* that is arranged between the input ports 106A, 106B and the measurement volume 104. The droplet generator 11*o* is configured to generate microdroplets of a first fluid (e.g. a sample fluid) in a second fluid (e.g. a carrier fluid), in particular monodisperse microdroplets having a uniform size. For this, the droplet generator 11*o* may for example comprise a T-junction at which a first channel from the first input port 106A intersects under an angle with a second channel from the second input port 106B, wherein an outlet of the T-junction is in fluid communication with the measurement volume 104. This may allow for generating microdroplets of a sample fluid provided at the first input port 106A in a carrier fluid provided at the second input port 106B. In other examples, the droplet generator 11*o* may have a different design and may e.g. be configured to generate the microdroplets by co-flow droplet generation, by hydrodynamic flow focusing, and/or by step emulsification. In other embodiments, the sensor chip 100 may not comprise the droplet generator 110, but a carrier fluid that already contains sample objects may be provided to the sensor chip 100 via an input port.

The measurement volume 104 is configured to receive a carrier fluid comprising a plurality of sample objects 112. In the example of FIG. 1*a*, 1*b*, the sample objects 112 are the microdroplets of the sample fluid in the carrier fluid that are generated by the droplet generator 110, e.g. to study properties of the sample fluid or objects or substances contained therein. In other embodiments, the sample objects 112 may for example be microbubbles or microparticles such as microbeads, e.g. agarose beads. To generate the microdroplets 112, a carrier fluid that is immiscible with the sample fluid may be used such that the carrier fluid and the microdroplets from an emulsion, e.g. as detailed below for method 500. Additionally or alternatively, surfactants such as amphiphilic molecules may be admixed to the sample fluid and/or to the carrier fluid, e.g. such that a shell layer 112B, for example a lipid bilayer, is formed around a core 112A of the microdroplets 112 as illustrated in FIG. 1*b*, wherein the core 112A of a microdroplet 112 contains the respective sample, e.g. an amount of sample fluid. The microdroplets 112 may have an identical composition or may have different compositions, e.g. by varying a composition of the sample fluid over time, e.g. a concentration of one or more objects or substances in the sample fluid. A physical dimension of the sample objects or microdroplets 112 such as a width or a diameter d may for example be between 10 μm and 100 μm.

The sensor chip 100 further comprises a sensing layer 102C in or on the lower substrate 102C and adjacent to the measurement volume 104. A plurality of sensing elements 115A, 115B are arranged in the sensing layer 102C, each of which is configured to generate a sensor signal, e.g. an optical or electrical sensor signal, characterizing a physical observable in the vicinity of the respective sensing element 115A, 115B, e.g. at the position of the respective sensing element 115A, 115B. Each of the sensing elements 115A, 115B may for example be an optically addressable solid-state spin system 115A (e.g. a nitrogen-vacancy center) or a microelectrode 115B as illustrated in the insets below FIG. 1*b*.

The sensing elements are grouped into a plurality of spatially separated sensors 114A/114B for probing the samples 112A, which are illustrated by the dotted rectangles in FIGS. 1*a*, 1*b*. Each of the sensors 114A/114B may for example be a sensing region 114A in the sensing layer 102C, wherein the sensing region 114A comprises a plurality of solid-state spin systems 115A and is separated from adjacent sensing regions 114A by portions of the sensing layer 102C that do not comprise solid-state spin systems or comprise a smaller density of solid-state spin systems. In another example, each of the sensors 114A/114B may for example be a sensor 114B comprising a single sensing element such as a single microelectrode 115B. In some examples, the sensor chip 100 may also comprise sensors and/or sensing elements of different types, e.g. a combination of microelectrodes and solid-state spin systems. In the following, the sensors 114A/114B in the sensing layer 102C are referred to as sensors 114, wherein each sensor 114 may e.g. be a sensing region 114A or a sensor 114B as described above. Accordingly, the sensing elements 115A/115B may also be referred to as sensing elements 115.

The sensors 114 are arranged in a periodic array in the bottom wall 104-A of the measurement volume 104. In the example of FIGS. 1*a*, 1*b*, the sensors 114 are arranged in a one-dimensional array or linear chain with a spacing $a_1$ between adjacent sensors 114, wherein the spacing $a_1$ is measured between the centers of the respective sensors 114. A unit cell 116 of the sensor array, i.e. the fundamental unit of which the array may be formed by successive tiling, may for example be defined as a square of length $a_1$ that is centered around a respective sensor as illustrated by the thick dashed line in FIG. 1*a*.

Each of the sensors 114 is configured to generate a common sensor signal that characterizes a physical observable in the vicinity of the respective sensor 114, e.g. at the position of the respective sensor 114. The common sensor signal of a sensor 114 may for example correspond to a sum or an average of the sensor signals of the sensing elements 115 of the respective sensor 114 or may correspond to the sensor signal of a sensing element 115 if the respective sensor 114 only contains a single sensing element. A value of the physical observable characterized by the common sensor signal of a sensor 114 may be sensitive to changes in a sensing volume surrounding the sensor 114, wherein at least a part of the sensing volume overlaps with a portion of the measurement volume 104, and may thus allow for probing properties of the samples 112A. In the example of FIG. 1*b*, the sensors 114 are fully embedded in the lower substrate 102A such that the sensors 114 and the sensing elements 115 therein are not exposed to the measurement volume. In other examples, the sensors 114 may also be exposed to the measurement volume 104, e.g. such that some or all of the sensing elements 115 are exposed to the measurement volume 104. A surface of the sensors 114 or sensing element 115 may for example be flush with the top surface of the lower substrate 102A or may protrude from the top surface of the lower substrate 102A. In some examples, the sensors 114 may also be arranged in the cover 102B instead of the lower substrate 102A.

In a preferred embodiment, each of the sensors 114 is a magnetic quantum sensor that comprises a plurality of optically addressable solid-state quantum systems 115A arranged in a sensing region 114A as illustrated in the left inset below FIG. 1*b*. In particular, a surface layer of the lower substrate 102A adjacent to the measurement volume 104 such as the sensing layer 102C or the entire lower substrate 102A is a slab of diamond. In the sensing layer 102C, a plurality of nitrogen-vacancy centers is embedded in the diamond crystal structure as the sensing elements 115A, thereby forming the sensing regions 114A. The NV centers may in particular be in a negative charge state, which exhibits a triplet electronic ground state with a spin of S=1. The spin state of the NV centers may be manipulated using microwaves and may be read-out and/or initialized via optical transitions to an excited triplet state, e.g. through spin-dependent fluorescence in the excited state. This allows for using NV centers as nanoscale magnetometers for measuring magnetic fields, for example through optically detected magnetic resonances (ODMR).

In other embodiments, different types of sensing elements may be used, for example temperature sensing elements, current sensing elements, voltage sensing elements, inductive sensing elements, and/or capacitive sensing elements. In some examples, each of the sensors 114 may e.g. comprise one or more electrodes 115B as illustrated in the right inset below FIG. 1*b*, wherein the electrodes 115B may be exposed to the measurement volume 104.

The sensor chip 100 comprises two or more boundary or guiding structures that are configured to confine or guide a motion of the sample objects 112 in the measurement volume 104 in order to align the sample objects 112 with the sensor array. In the example of FIG. 1*a*, 1*b*, two opposing sidewalls 104-1, 104-2, which extend between the bottom wall 104-A and the top wall 104-B of the measurement volume 104 and may e.g. correspond to the sidewalls of the recess in the lower substrate 102A, form the boundary or guiding structures. The sidewalls 1041, 104-2 extend parallel to each other along the X axis and are separated by a distance D. The distance D is chosen such that it matches the spacing $a_1$ of the sensor array. Furthermore, the sidewalls 104-1, 104-2 are arranged such that the sensors 114 are centered between the sidewalls 104-1, 104-2 and the sidewalls 104-1, 104-2 thus are aligned with two opposing edges of each unit cell 116 of the sensor array.

In this way, when the measurement volume 104 is completely filled with objects such as the sample objects 112 having a circular cross section with a diameter d corresponding to the spacing $a_1$, e.g. such that the entire bottom wall 104-A is covered by the sample objects 112, the sidewalls 104-1, 104-2 cause the sample objects 112 to arrange in a self-organized structure in which each of the sample objects 112 is aligned with a respective one of the sensors 114, e.g. such that the sample object 112 is centered within the respective unit cell 116 as illustrated in FIG. 1*a*. In the self-organized structure, the sample objects 112 form a close-packing of equal circles, in which each of the sample objects 112 is in contact with the sidewalls 104-1, 104-2 as well as with other sample objects 112. In some examples, the sample objects 112 may have a spherical shape as illustrated in FIGS. 1*a*, 1*b* and the self-organized structure may correspond to a close-packing of equal spheres. In the self-organized structure, interactions between the sample objects 112 and the sidewalls 104-1, 104-2 and interactions between the sample objects 112 themselves prevent all sample objects 112 apart from the sample objects arranged at the edges of the self-organized structure from moving within the measurement volume 104, thereby ensuring a stable positioning relative to the respective sensor 114. In some embodiments, the sensor chip 100 may further comprise boundary or guiding structures (not shown) that prevent the self-organized structure or sample objects arranged at the edges thereof from moving along the direction of flow in the measurement volume 104.

In the example of FIG. 1*b*, the height of the measurement volume 104 also corresponds to the spacing $a_1$ such that the spherical sample objects 112 are in contact with both the bottom wall 104-A and the top wall 104-B, thereby ensuring that the sample objects 112 are adjacent to the sensors 114 along the Z direction of FIG. 1*b*, which may also be referred to as the vertical direction. In other examples, the height of the measurement volume 104 may be larger than the spacing $a_1$ or the measurement volume 104 may be open from the top, e.g. when the cover 102B is not present. In such cases, the position of the sample objects 112 along the vertical direction may for example be controlled by controlling a fill level of the carrier fluid in the measurement volume 104 and/or by using a carrier fluid having a lower density than the sample objects 112. In some examples, the sample objects 112 may not be spherical, but may nonetheless have a circular cross section in the XY plane of FIG. 1*a* with a diameter d and may e.g. have a spheroidal, ellipsoidal or cylindrical shape. The height of the measurement volume 104 may for example be smaller than the spacing $a_1$. In yet other examples, the sample objects 112 in the self-organized structure may not have a circular cross section, but the self-organized structure may nonetheless resemble a close-packing of equal circles, e.g. in the sense that centers of the sample objects and/or contact points between the sample objects are aligned with the corresponding points in an ideal close-packing of equal circles.

FIG. 2 depicts a schematic illustration (not to scale) of a sensor chip 200 for parallelized probing of a plurality of samples according to another exemplary embodiment of the invention in top view.

The sensor chip 200 is similar to the sensor chip 100 of FIGS. 1*a*, 1*b* and also comprises a substrate 102, in which a measurement volume or measurement chamber 104 is arranged for receiving a carrier fluid comprising a plurality of sample objects 112 such as microdroplets or cells. In the example of FIG. 2, the measurement volume has a rectangular shape with a first pair of opposing sidewalls 104-1, 104-2 being separated by a first distance $D_1$ and a second pair of opposing sidewalls 104-3, 104-3 being separated by a second distance $D_2$. The first and seeond distances may for example each be between 100 μm and 2 mm. A bottom wall of the measurement volume 104 extends between the sidewalls 104-1 to 104-4, wherein a top surface of the bottom wall, which is exposed to the measurement volume 104, is a flat surface that does not comprise any protrusions or depressions. In some embodiments, the bottom wall and/or one or more of the sidewalls 104-1 to 104-4 may be coated with a hydrophilic or hydrophobic coating, e.g. to facilitate or prevent wetting of the respective surface by a carrier fluid. The respective coating may in particular be a uniform coating that is applied to the entire surface and is not patterned or structured in any way.

Similar to the sensor chip 100, the sensor chip 200 comprises two input ports 106A, 106B and an output port 108 as well as a droplet generator 11*o* that is arranged between the input ports 106A, 106B and the measurement volume 104. The sensor chip 200 further comprises a microfluidic inlet channel 202 that is arranged between the droplet generator 110 and the measurement volume 104 for providing the carrier fluid comprising the microdroplets 112 generated by the droplet generator 110 to the measurement volume 104. The sensor chip 100 also comprises a microfluidic outlet channel 204, which connects the measurement volume 104 to the output port 108. Along the outlet channel 204, a microfluidic valve 206 is arranged, wherein the valve 206 is configured to adjust a cross-sectional area of the outlet channel 204, e.g. to selectively prevent sample objects 112 from leaving the measurement volume 104 via the outlet channel 204 while permitting a flow of the carrier fluid through the outlet channel 204.

In the bottom wall of the measurement volume 104, a plurality of sensors 114 are arranged in a two-dimensional periodic array, wherein each of the sensors 114 comprises one or more sensing elements (not shown), e.g. as described above with reference to FIGS. 1*a*, 1*b*. In the example of FIG. 2, the two-dimensional periodic array is a hexagonal lattice with a spacing $a_h$ between neighboring sensors 114. The hexagonal lattice is spanned by the primitive vectors $\vec{\alpha}_1=(\alpha_h, O)$ and $\vec{\alpha}_2=(\alpha_h/2, \sqrt{3}\, a_h/2)$ connecting the centers of adjacent sensors 114 as illustrated by the respective arrows in FIG. 2. A unit cell 116 of the hexagonal lattice, in which a respective one of the sensors 114 is arranged, has a hexagonal shape as illustrated by the thick dashed line in FIG. 2.

The sidewalls 104-1 to 104-4 of the measurement volume 104 constitute boundary or guiding structures that are configured to confine or guide a motion of the sample objects 112 in the measurement volume 104. The distances $D_1$ and $D_2$ are chosen such that a uniform close-packing of equal circles or spheres (e.g. cylindrical or spherical sample objects 112) having a diameter corresponding to the spacing $a_h$ of the sensor array can be arranged in the measurement volume 104 with the outermost circles/spheres being in contact with the sidewalls 104-1 to 104-4. When the entire bottom wall of the measurement volume 104 is covered by the circles/spheres as illustrated in FIG. 2, the position of each of the circles/spheres is fixed either by contact with other circles/spheres surrounding the respective circle/sphere or by contact with neighboring circles/spheres as well as with one or more of the sidewalls 104-1 to 104-4. The resulting self-organized structure is thus stable since—with the exception of the circles/spheres located at the orifices of the inlet and outlet channels 202, 204—none of the circles/spheres can move without moving at least one other circle/sphere i.e. the translational degrees of freedom of the circles/spheres parallel to the bottom wall of the measurement volume 104 are eliminated. In some examples, the inlet and outlet channels 202, 204 may also be filled with spheres to prevent the circles/spheres at the orifices of the inlet and outlet channel 202, 204 from moving.

In the example of FIG. 2, the distance $D_1$ between the sidewalls 104-1, 104-2, which extend parallel to the primitive vector $\vec{\alpha}_1$ of the sensor array, is equal to $(1+\sqrt{3}\, N_1/2)\cdot a_h$ with $N_1$ being a positive integer greater than 1 such that exactly $(N_1+1)$ one-dimensional chains of circles or spheres extending parallel to the sidewalls 104-1, 104-2 can be arranged between the sidewalls 104-1, 104-2 in a uniform close-packing of equal circles or spheres. The distance $D_2$ between the sidewalls 104-3, 104-4, which extend perpendicular to the sidewalls 104-1, 104-2, is equal to $(N_2+1)\cdot a_h$ with $N_2$ being a positive integer greater than 1 such that one-dimensional chains of length $(N_2+1)$ extending perpendicular to the sidewalls 104-3, 104-4 can be arranged between the sidewalls 104-3, 104-4. The integers N, and $N_2$ may for example each be between 9 and 99. In other examples, the measurement volume 104 may have a different shape and the sidewalls 104-1 to 104-4 may for example form a parallelogram. In particular, each pair of sidewalls may extend parallel to a respective one of the primitive vectors $a_1$, $a_z$ and may be separated by a distance $D_1=(1+\sqrt{3}\, N_1/2)\cdot a_h$, and $D_2=(1+\sqrt{3}\, N_2/2)\cdot a_h$, respectively. In yet other examples, opposing sidewalls may not be parallel to each other and/or the number of sidewalls may be different. The measurement volume 104 may for example also have a triangular or hexagonal shape.

The hexagonal lattice in which the sensors 114 are arranged is specifically adapted to the arrangement of objects having a circular cross section such as spheres in a uniform close-packing of equal circles or spheres in two dimensions, which also constitutes a hexagonal lattice. Moreover, the position of the sidewalls 104-1 to 104-4 is chosen such that the hexagonal lattice in which the sensors 114 are arranged and the hexagonal lattice of the close-packing of equal circles or spheres are aligned with each other, e.g. such that the unit cells of the two lattices are aligned with each other in a direction of view perpendicular to the bottom wall of the measurement volume 104. In this way, each of the circles/spheres or sample objects 112 in the measurement volume may be arranged above a respective one of the sensors 114, e.g. such that the edges of the respective unit cell 116 are tangential to a circumference of the sphere in the direction of view perpendicular to the bottom wall and a center of the circle/sphere is aligned with a center of the corresponding sensor 114. This may for example be achieved by arranging the sidewalls 104-1 to 104-4 such that each of the outermost sensors 114 of the array is separated by a distance of $a_h/2$, corresponding to a radius of the circles/spheres, from the respective sidewall.

FIGS. 3*a* and 3*b* depict schematic illustrations (not to scale) of a sensor chip 300 and a sensor chip 310, respectively, for parallelized probing of a plurality of samples according to other exemplary embodiments of the invention in top view. The sensor chips 300, 310 are similar to the sensor chip 200 and also comprise a substrate 102 with a measurement volume 104, a droplet generator 11*o* with two input ports, and an output port 108.

The sensor chip 300 of FIG. 3*a* comprises a rectangular measurement volume 104 formed by a bottom wall with a flat top surface that extends between two pairs of opposing sidewalls. On the bottom wall, a plurality of guiding walls 302 are arranged, which extend upwards from the top surface of the bottom wall, e.g. towards a top wall or opening of the measurement volume 104. In some embodiments, upper portions of the guiding walls 302 may be in contact with top wall, i.e. the guiding walls 302 may extend from the bottom wall to the top wall. The guiding walls 302 are parallel to a pair of opposing sidewalls and are arranged in an alternating zig-zag pattern. In the alternating zig-zag pattern, every other guiding wall 302 is in contact with a first sidewall 104-3 of the other pair of opposing sidewalls of the measurement volume 104 while leaving an opening or cutout adjacent to a second sidewall 104-4 of the measurement volume 104 opposing the first sidewall 104-3, whereas the remaining guiding walls 302 are in contact with the second sidewall 104-4 while leaving an opening or cutout adjacent to the first sidewall 104-3. Thereby, the guiding walls 302 partition the measurement volume 104 into a meandering channel that extends from an inlet of the measurement volume 104 to an outlet of the measurement volume 104.

In the bottom wall of the measurement volume 104, a plurality of sensors 114 are arranged in a two-dimensional rectangular array having a first spacing $a_1$ along the X direction of FIG. 3*a* and a second spacing $a_2$ along the Y direction, wherein the second spacing is larger than the first spacing. Each of the sensors 114 along the circumference of the sensor array, i.e. the outermost sensors of the sensor array, is arranged at a distance of $a_1/2$ from a sidewall of the measurement volume 104. The sidewalls 104-3, 104-4 are separated by a distance $D_2$ that is equal to an integer multiple of $a_1$, $D_2=M\cdot a_1$, wherein M may for example be between 10 and 100. Furthermore, the guiding walls 302 are arranged such that the meandering channel has a width equal to the first spacing $a_1$ and a center line of the channel is aligned with a center of the sensors 114, e.g. similar to the sensor chip 100 of FIG. 1. In this way, objects having a circular cross section such as spherical or cylindrical sample objects 112 in the measurement volume 104 may be confined to a close-packing of equal circles or spheres in a rectangular lattice as opposed to the hexagonal lattice of the uniform close-packing of equal circles or spheres as e.g. in FIG. 2, thus matching the rectangular lattice of the sensor array. This may for example be advantageous for reducing cross-talk between the sensors 114 due to the increase spacing $a_2$ as well as for facilitating formation of a corresponding self-organized structure of sample objects 112 due to the additional confinement provided by the guiding walls 302. In some embodiments, the sensor chip 300 may comprise hydrophilic or hydrophobic coatings instead of or in addition to the guiding walls 302, e.g. similar to the sensor chip 310.

The sensor chip 310 of FIG. 3*b* comprises a measurement volume 104 having a rectangular center portion 104*b* arranged between a proximal portion 104*a* and a distal portion 104*c* of the measurement volume 104. The center portion 104*b* is formed by two opposing parallel sidewalls extending parallel to the X axis of FIG. 3*b*, whereas the proximal and distal portions 104*a*, 104*c* are tapered such that a width of the proximal and distal portions 104*a*, 104*c* perpendicular to the sidewalls of the center portion 104*b*, i.e. along the Y direction of FIG. 3*b*, increases from an inlet orifice and an outlet orifice, respectively, of the measurement volume 104 towards the center portion 104*b*.

In the center portion 104*b* of the measurement volume 104, a plurality of coatings 312 are arranged on a bottom wall of the measurement volume 104. The coatings 312 may for example be hydrophilic or hydrophobic coatings on a top surface of the bottom wall and may for example be configured to prevent wetting of the respective regions by the carrier fluid comprising the sample objects 112, thereby forming boundary or guiding structures that make a portion of the top surface of the bottom wall inaccessible to the carrier fluid and the sample objects 112. The coatings 312 extend parallel to the sidewalls of the center portion 104*b* and define a plurality of parallel channels that extend through the center portion 104*b* from the proximal portion 104*a* to the distal portion 104*c*. In some embodiments, the sensor chip 310 may also comprise guiding walls instead of or in addition to the coatings 312, e.g. similar to the sensor chip 300.

In the bottom wall of the measurement volume 104, a plurality of sensors 114 are arranged in a two-dimensional rectangular array with first and second spacings $a_1$ and $a_2$ similar to the sensor arrangement of the sensor chip 300 of FIG. 3*a*, e.g. such that the sensor array 114 covers the entire center portion 104*b*. The coatings 312 are arranged such that each of the channels has a width corresponding to the first spacing $a_1$ and that the sensors 314 along each channel are centered relative to a center line of the respective channel. The angle between the sidewalls of the tapered proximal portion 104*a*, the angle between the sidewalls of the tapered distal portion 104*c* as well as the lengths of the channels are chosen such that when the measurement volume 104 is filled with objects having a circular cross section such as spherical or cylindrical sample objects 112, the sample objects 112 form a self-organized close-packing in which each sample object 112 in the center portion 104*b* is arranged above a respective one of the sensors 114. The proximal and distal portions 104*a*, 104*c* may not comprise any sensors 114, but the sample objects 114 arranged therein may ensure the correct positioning of the sample objects 114 in the center portion 104*b* relative to the sensors 114 by forming a close-packing of circles or spheres that prevents sample objects 114 at the end portions of the channels from moving and in particular leaving the channels.

FIG. 4 depicts a schematic illustration (not to scale) of a measurement system 400 for parallelized probing of a plurality of samples according to an exemplary embodiment of the invention in side view. The measurement system 400 may be configured for use with a sensor chip according to any one of the embodiments described herein, e.g. one or more of the sensor chips 100, 200, 300, and 310. Additionally or alternatively, the measurement system 400 may also be configured for use with a sensing device according to any one of the embodiments described herein, e.g. the sensing device 700 of FIGS. 7*a*, 7*b* described below. The measurement system 400 may be used for executing a method for parallelized probing of a plurality of samples according to any one of the embodiments described herein, e.g. the method 500 described below with reference to FIG. 5 or the method 800 described below with reference to FIG. 8.

The measurement system 400 comprises a mount 402 that is configured to receive a sensor chip 404. The sensor chip 404 comprises a sensing layer 102C arranged in or on a substrate, wherein the sensing layer 102C comprises a plurality of sensing elements (not shown). The sensing elements may e.g. form a periodic array of sensors 114 as illustrated in FIG. 4, for example as detailed above with reference to FIGS. 1*a*, 1*b*. The sensor chip 404 further comprises a measurement volume 104 adjacent to the sensing layer 102C. In some embodiments, the sensor chip 404 may correspond to one of the sensor chips 100, 200, 300, and 310 described above. In other embodiments, the sensor chip 404 may correspond to the sensor chip 704 of the sensing device 700 described below with reference to FIG. 7. The mount 402 is configured to hold the sensor chip 404 and may for example comprise means for removably attaching the sensor chip 404 to the mount 404, e.g. one or more fastening clips or screws. In some embodiments, the mount 402 may also be configured to move the sensor chip 404 along one or more directions and/or to tilt the sensor chip 404 around one or more axes, e.g. for alignment purposes. In some embodiments, the mount 402 may be similar to the mount 702 of the sensing device 700 of FIGS. 7*a*, 7*b*.

The measurement system 400 further comprises a microfluidics unit 406 that is configured to provide a carrier fluid comprising a plurality of sample objects 112 to the measurement volume 104 of the sensor chip 404. In the example of FIG. 4, the microfluidics unit 406 is configured to be connected to an input port 106 of the sensor chip 404 that is in fluid communication with the measurement volume 104. The microfluidics unit 406 may for example comprise one or more reservoirs (not shown) for storing fluids such as a carrier fluid and a sample fluid. The microfluidics unit 406 may also comprise one or more pumps (not shown) for supplying the respective fluids to the sensor chip 404. The microfluidics unit 406 may further comprise a droplet generator (not shown) for generating microdroplets of the sample fluid in the carrier fluid, e.g. similar to the droplet generator 11*o* of the sensor chip 100 of FIG. 1. In other examples, the microfluidics unit 406 may not comprise a droplet generator, but may e.g. be configured to supply the carrier fluid and the sample fluid to a droplet generator on the sensor chip 404. The microfluidics unit 406 may further be configured to be connected to output ports 108A, 108B of the sensor chip 404, e.g. to remove the carrier fluid and the sample objects 112 from the sensor chip 404.

The measurement system 400 comprises a measurement device 408 that is configured to read out electrical or optical sensor signals from the sensing elements on the sensor chip 404. The measurement system 400 may e.g. be configured to a read out a common sensor signal from each of the sensors 114 in the sensor array of the sensor chip 404. The measurement device 408 may for example be configured to be connected to an electrical connector (not shown) on the sensor chip 404 in order to provide an electrical connection between the sensors 114 and the measurement device 408. The measurement device 408 may comprise a plurality of detectors or measuring elements 410, each of which may be configured to read out the common sensor signal from a respective one of the sensors 114. Each of the measuring elements 410 may for example comprise a voltmeter and/or an ammeter for measuring a voltage and a current, respectively, associated with the respective sensor 114. In other embodiments, the measuring elements 410 may e.g. be photosensitive detectors as detailed below.

The measurement system 400 also comprises a controller 412, wherein the controller 412 may be implemented in hardware, software, or a combination thereof. The controller 412 may in particular comprise a processor (not shown) and a memory (not shown), wherein the memory stores instructions that can be executed by the processor to provide the functionality described herein. The controller 412 may e.g. comprise a central processing unit (CPU), a graphics processing unit (GPU), an application-specific integrated circuit (ASIC), a field-programmable gate array (FPGA), a non-volatile memory, a volatile memory, a microcontroller, and/or a system-on-a-chip (SoC). Additionally or alternatively, the controller 412 may also comprise other analog and/or digital electronic circuits. In some examples, the measurement device 408 may be integrated into the controller 412 at least in part.

The controller 412 is configured to control the microfluidics unit 406 to control a number of sample objects 112 in the measurement volume 104, e.g. by providing a control signal for a pump and/or a valve of the microfluidics unit 406 to generate a flow of the carrier fluid comprising the sample objects 112 to the measurement volume 104. The controller 412 is in particular configured to control the microfluidics unit 406 to control the number of sample objects 112 in the measurement volume such that the sample objects 112 form a self-organized structure in the measurement volume 104, for example a self-organized structure in which a respective sample object 112 is arranged adjacent to each of the sensors 114, e.g. as detailed below for method 500. The controller 412 is further configured to control the measurement device 408 to perform a measurement on one or more of the samples 112A while the sample objects 112 are arranged in the self-organized structure, wherein a measurement on a sample is performed using one or more sensing element arranged adjacent to the respective sample object in the self-organized structure, e.g. as detailed below for methods 500 and 800. In some embodiments, the controller 412 may be configured to execute some or all of the steps of a method for parallelized probing of a plurality of samples according to any one of the embodiments described herein, e.g. the method 500 and/or the method 800.

In the example of FIG. 4, the sensors 114 on the sensor chip 404 are magnetic quantum sensors, in particular magnetic quantum sensors comprising optically addressable solid-state quantum systems such as nitrogen-vacancy centers in diamond, e.g. as detailed above for the sensor chip 100 of FIGS. 1*a*, 1*b*. For manipulating the solid-state quantum systems, e.g. for optically exciting the solid-state quantum systems, the measurement system 400 is configured for use with one or more light sources 414, in particular lasers, that are configured to generate light at one or more absorption wavelengths of the solid-state quantum systems for illuminating the sensors 114. The one or more light sources 414 may be provided as independent units or may be part of the measurement system 400 in some embodiments. The measurement system 400 may further comprise an illumination system (not shown) that is configured to couple a light beam generated by the one or more light sources 414 into an optical illumination path that extends through the sensor chip 404 and sequentially intersects with some or all of the sensors 114, e.g. such that solid-state quantum systems in each of the sensors 114 can be excited with a single beam of light that passes through the sensors 114 one after the other. Along the illumination path, the light may for example be reflected off surfaces of the sensor chip 404, e.g. by total internal reflection and/or at reflective coatings on the respective surfaces. In some examples, the illumination system of the measurement system 400 may be similar to the illumination system 706 of the sensing device 700. The measurement system 400 may comprise additional components for manipulating the solid-state quantum systems, for example a magnet (not shown) for applying a bias magnetic field to the sensor chip 404 and/or a microwave and/or radio-frequency antenna (not shown) for applying a microwave or radio-frequency signal to the sensor chip 404.

In this example, the measurement device 408 is a multichannel photodetector comprising a plurality of photosensitive elements as the measuring elements 410. Each of the photosensitive elements 410 is configured to determine an intensity of light incident on the respective element and may for example comprise one or more photodiodes or photomultipliers or one or more pixels on a CCD or CMOS chip. Each of the photosensitive elements 410 is associated with a respective one of the sensors 114, wherein the measurement system 400 may comprise an imaging system (not shown) that is configured to collect light emitted by solid-state spin systems in the sensors 114 and image the light onto the respective photosensitive elements 410. In some embodiments, the measurement device 408 may comprise a camera chip with a plurality of photosensitive pixels and the controller 412 may be configured to select, for each of the sensors 114, a subset or region-of-interest from the plurality of photosensitive pixels as the respective photosensitive element 410, e.g. as detailed below for the sensing device 700 of FIG. 7 and the method 800 of FIG. 8.

The measurement system 400 further comprises a camera 416, which in the example of FIG. 4 is arranged opposite to the measurement device 408. The camera 416 is configured to take images of the sample objects 112 on the sensor chip 404, which may for example be used for tracking sample objects 112 on the sensor chip 404 and/or for monitoring formation of the self-organized structure of sample objects 112 in the measurement volume 104. In some examples, the controller 412 may be configured to automatically track sample objects 112 on the sensor chip 404 using the camera 416, e.g. using computer-vision techniques. In other examples, the controller 412 may be configured to provide images obtained from the camera 416 to a user for manual tracking and/or monitoring. In some embodiments, the measurement device 408 may also be used as a camera for taking images of the sample objects 112.

In the example of FIG. 4, the sensor chip 404 further comprises a sorting unit 418 that is arranged along an outlet channel of the sensor chip 404 and configured to sort sample objects 112, e.g. by selectively diverting sample objects 112 to either one of two output ports 108A, 108B of the sensor chip 404. The sorting unit 418 may for example comprise one or more electrodes for generating an electric field, one or more inductive elements for generating a magnetic field, one or more optical elements or light sources for generating an optical potential, and/or one or more microfluidic elements such as valves and/or channels for generating a diverting flow. The controller 412 is configured to control the sorting unit 418 and may in particular be configured to control the sorting unit 418 in order to sort the sample objects 112 based on measurement results obtained using the sensors 114, e.g. by diverting sample objects 112 associated with a measurement value above a threshold to the first output port 108A and sample objects 112 associated with a measurement value below the threshold to the second output port 108B.

FIG. 5 shows a flow diagram of a method 500 for parallelized probing of a plurality of samples in accordance with an exemplary embodiment of the invention. The method 500 may for example be implemented with one of the sensor chips 100, 200, 300, 310, 404, 704, with the measurement system 400, and/or with the sensing device 700. In the following, the method 500 will be described using the sensor chip 200 and the system 400 as a non-limiting example for illustration purposes. The method 500 is not limited to the order of execution indicated by the flow diagram of FIG. 5. As far as technically feasible, the method 500 may be executed in an arbitrary order and steps thereof may be executed simultaneously at least in part, e.g. steps 504, 506 and 508 described below.

The method 500 comprises, in step 502, providing a sensor chip with a sensing layer arranged in or on a substrate and a measurement volume adjacent to the sensing layer, wherein the sensing layer comprises a plurality of sensing elements. For example, a sensor chip such as the sensor chip 200 comprising a periodic array of sensors 114 arranged in a substrate 102 and a measurement volume 104 adjacent to the sensor array may be provided. The sensor chip 200 may for example be mounted in the mount 402 of the measurement system 400. In embodiments in which the samples 112A or sample objects 112 have a pre-determined size, e.g. when probing cells or microdroplets of a pre-determined size, a spacing of the sensors 114 on the sensor chip 200 may be specifically adapted to the samples 112A or sample objects 112, e.g. by providing a sensor chip 200 for which the spacing $a_h$ corresponds to a physical dimension of the sample objects 112.

In step 504, a carrier fluid comprising a plurality of sample objects 112 is provided to the measurement volume 104 of the sensor chip 200. Each of the sample objects 112 comprises or forms a respective sample 112A, which may for example be an amount of a sample fluid such as a biological sample fluid, which may e.g. comprise biological samples such as proteins, DNA, bacteria, cells or parts thereof, or a chemical sample fluid, which may e.g. comprise one or more reagents and/or products of a chemical reaction. In one example, each of the sample objects 112 is a microdroplet comprising a cell or a bacterium in a sample fluid, wherein the cells or bacteria are configured to produce a substance such as ethanol. The method 500 may be used to assess how efficient the cells or bacteria are in producing the substance, e.g. to select the most efficient cells or bacteria from a plurality of cells or bacteria. The measurement performed in step 508 may be used to determine a concentration of the substance in the microdroplets. Solid-state spin systems such as nitrogen-vacancy centers may for example be allow for determining a concentration of ethanol in the microdroplets by nuclear magnetic resonance spectroscopy.

Providing the carrier fluid comprising the plurality of sample objects 112 may in particular comprise generating a plurality of microdroplets of the sample fluid in the carrier fluid, e.g. using the droplet generator no of the sensor chip 200 or a droplet generator of the microfluidics unit 406. In this example, the microdroplets may constitute the sample objects 112. For this, a carrier fluid may be used that is immiscible with the sample fluid. The sample fluid may for example be an aqueous solution or suspension and the carrier fluid may be an oil (or vice-versa), for example a hydrocarbon oil (e.g. hexadecane), a fluorocarbon oil (e.g. octadecafluor-odecahydro naphthalene or 1-(1,2,2,3,3,4,4,5,5,6,6-undecafluorocyclohexyl)ethanol), a silicone oil, or a mineral oil, e.g. as described in EP 2 270 236 B1. In another example, the sample fluid may be a first oil and the carrier fluid may be a second oil that is immiscible with the first oil, e.g. silicone oil and mineral oil or hydrocarbon oil and fluorocarbon oil. To stabilize the microdroplets, surfactants such as amphiphilic compounds may be added to the sample fluid and/or the carrier fluid, for example one or more of a polyethylene glycol-perfluoropolyether (PEG-PFPE) block copolymer fluorinated surfactant, Octoxinol 9 ($C_{14}H_{22}O(C_2H_4O)_n$, Triton X-100), sodium dodecyl sulfate (SDS), sorbitan monooleate ($C_{24}H_{44}O_6$, Span 80), and glyceryl monooleate ($C_{21}H_{40}O_4$, monoolein), e.g. as described in J.-L. Baret, *Lab Chip,* 2012, 12, 422-433. The surfactants may form a shell layer 112B around the core 112A of each microdroplet and thereby may for example prevent the microdroplets from merging. A physical dimension of the microdroplets may be adapted to a spacing of the sensor array of the sensor chip 200, e.g. such that a diameter of the microdroplets corresponds to the spacing $a_h$. The size of the microdroplets may for example be controlled by adjusting a flow velocity of the carrier fluid and/or of the sample fluid in the droplet generator and/or by adjusting a composition of the carrier fluid and/or the sample fluid.

In step 506, a number of the sample objects 112 in the measurement volume 104 is controlled such that the sample objects 112 form a self-organized structure, e.g. a self-organized periodic structure, in the measurement volume 104. In the self-organized structure, a respective sample object 112 may for example be arranged adjacent to each of the sensors 114 on the sensor chip 200. For example, a flow of the carrier fluid comprising the microdroplets 112 may be generated through the inlet channel 202 to supply microdroplets 112 to the measurement volume 104, thereby successively filling up the measurement volume 104. At the same time, carrier fluid may be removed from the measurement volume 104 through the outlet channel 204, wherein the valve 206 may be set such that the microdroplets 112 cannot pass through the valve 206. In this way, the number of microdroplets 112 in the measurement volume 104 may be increased step by step.

As the number of microdroplets 112 in the measurement volume 104 is increased, the microdroplets 112 may come in contact with each other as well as with the boundary structures in the form of the sidewalls 104-1 to 104-4. The interactions between the microdroplets 112 themselves and the interaction between the microdroplets 112 and the sidewalls 104-1 to 104-4 lead to the formation of a self-organized close-packing as depicted in FIG. 2 when the entire bottom wall of the measurement volume 104 is covered by microdroplets 112. As detailed above with reference to FIG. 2, the sensors 114 in the array are arranged in a hexagonal lattice, which is adapted to the arrangement of circles or spheres in a uniform close-packing of equal circles/spheres, and the sidewalls 104-1 to 104-4 are arranged such that the self-organized close-packing of the microdroplets 112 is aligned with the sensor array, e.g. such that each of the microdroplets 112 in the measurement volume 104 is placed on top of a respective one of the sensors 114. In this self-organized periodic structure, each microdroplet 112 is pinned to its respective position since the neighboring microdroplets 112 and the sidewalls 104-1 to 104-4 prevent the microdroplet 112 from moving parallel to the bottom wall of the measurement volume. In some embodiments, the microdroplets 112 may comprise a monolayer of amphiphilic molecules, e.g. a lipid monolayer, as the shell layer 112A and a bilayer of amphiphilic molecules, e.g. a lipid bilayer, may be formed when neighboring microdroplets 112 come in contact with each other. This may further stabilize the self-organized periodic structure formed in the measurement volume 104.

In step 508, a measurement is performed on one or more of the samples 112A, in some embodiments on all of the samples 112A, while the sample objects 112 are arranged in the self-organized structure, wherein a measurement on a sample 112A is performed using one or more sensing elements 115 arranged adjacent to the respective sample object 112 in the self-organized structure. A measurement on a sample 112A may for example be performed using the sensor 114 on the sensor chip 200 adjacent to which the respective sample object 112 is arranged in the self-organized structure. The measurement on the one or more samples 112A may be performed in parallel, e.g. by reading out a measurement signal from each of the sensors 114 at the same time. The sample objects 112 in the self-organized structure may be stationary during the measurement, i.e. may not move relative to the sensors 114. This may also allow for repeating the measurement multiple times and/or performing a plurality of different measurements while the sample objects 112 remain adjacent to the respective sensor 114.

As detailed above with reference to FIGS. 1*a*, 1*b*, the sensors 114 may in particular be magnetic quantum sensors and may comprise optically addressable solid-state quantum systems 115A, e.g. nitrogen-vacancy centers in diamond, as the sensing elements 115. Performing a measurement may thus comprise illuminating the sensors 114 to optically polarize the solid-state quantum systems 115A, applying one or more microwave and/or radio-frequency pulses to the sensors 114 to manipulate a state of the solid-state quantum systems 115A, illuminating the sensors 114 to optically excite the solid-state quantum systems 115A, and/or performing an optical read-out of the state of the solid-state quantum systems 115A, e.g. by detecting an optical signal such as a fluorescence intensity emitted by the solid-state quantum systems 115A in the sensors 114. Optically addressable solid-state quantum systems may for example be used for performing nuclear magnetic resonance (NMR) spectroscopy.

The method 500 may further comprise rinsing the sensor chip 200 and in particular the measurement volume 104, e.g. after performing the measurement in step 508. For this, the measurement volume 104 may for example be rinsed with water or a buffer solution, for example to remove the sample objects 112 from the measurement volume 104. Subsequently, the method 500 may be repeated using the same sensor chip 200, e.g. to probe another set of samples.

FIG. 6 shows a microscopic image of a plurality of microdroplets 112 arranged in a self-organized periodic structure in a measurement volume 104 of a sensor chip according to an exemplary embodiment of the invention. The measurement volume 104 comprises two opposing sidewalls 104-1, 104-2, which are separated by a distance D=1300 μm. The measurement volume 104 is filled with monodisperse microdroplets 112 of a sample fluid comprising water in a carrier fluid comprising fluorocarbon oil, wherein the microdroplets 112 have a diameter d=104±2 μm. As a result of the surface-surface interactions between the microdroplets 112, the microdroplets 112 arrange in a self-organized periodic structure, namely a uniform close-packing of equal spheres forming a lattice with a hexagonal unit cell 116. The distance D between the sidewalls 104-1, 104-2 is chosen such that 14 linear chains of microdroplets 112 in the uniform close-packing of equal spheres can be arranged in the measurement volume 104, i.e. $D \approx (1+\sqrt{3} N/2) \cdot d$ with N=13. The self-organized periodic structure of microdroplets 112 is in contact with the sidewalls 104-1, 104-2, which break the translational symmetry of the uniform close-packing of equal spheres and pin the microdroplets 112 to predetermined positions within the measurement volume 104. The dashed arrows indicate a plurality of parallel laser beams, which may be used to excite optically addressable solid-state quantum systems of magnetic quantum sensors (not shown) arranged in a bottom wall underneath the measurement volume 104, e.g. as described in the following with reference to FIGS. 7*a*, 7*b*.

FIGS. 7*a* and 7*b* depict a schematic illustration (not to scale) of a sensing device 700 for parallelized probing of a plurality of samples according to an exemplary embodiment of the invention. FIG. 7*a* show the sensing device 700 in top view, whereas FIG. 7*b* shows a sensor chip 704 of the sensing device 700 in side view.

The sensing device 700 comprises a mount 702 that is configured to receive a sensor chip 704 of the sensing device 700. The mount 702 may for example comprise a frame with a recess or cutout that the sensor chip 704 can be arranged in. The frame may for example consist or comprise of metal, glass, plastic, or a combination thereof and preferably is configured to hold the sensor chip 704 such that the top and bottom surfaces of the sensor chip 704 are accessible, in particular for microscopic imaging. In some embodiments, the mount 702 may be similar to the mount 402 of the measurement system 400 of FIG. 4.

The sensor chip 704 comprises a substrate 102, which may for example be a slab of diamond. In or on the substrate 102, a measurement volume 104 is formed for receiving a carrier fluid comprising a plurality of sample objects 112, e.g. as detailed above for the sensor chip 100 of FIGS. 1*a*, 1*b*. The substrate 102 comprises a plurality of optically addressable sensing elements 115A, which are arranged in a sensing layer 102C adjacent to the measurement volume 104. The sensing layer 102C may for example be a surface layer of the substrate 102C, which forms a first or bottom wall 102-A of the measurement volume 104 as shown in FIG. 7*b*. In the example of FIG. 7*b*, the sensing elements 115A are optically addressable solid-state spin systems, in particular nitrogen-vacancy centers embedded in the diamond crystal structure of the sensing layer 102C. A depth of the sensing layer 102C perpendicular to the bottom wall 104-A of the measurement volume 104 may for example be between 5 μm and 10 μm.

Preferably, the NV centers are distributed throughout the sensing layer 102C as this simplifies fabrication of the sensor chip 704. A density of the NV centers in the sensing layer 102C may for example be uniform and may e.g. be between $10^{15}$ $cm^{-3}$ and $10^{18}$ $cm^{-3}$, in one example between $10^{16}$ $cm^{-3}$ and $10^{17}$ $cm^{-3}$. In other examples, the NV centers may be confined to spatially separated sensing regions 114A, which may e.g. form an array of sensors as detailed above for the sensor chip 100 of FIG. 1*a*, 1*b* and the sensor chip 200 of FIG. 2. A density of the NV centers within the sensing regions 114A may for example be at least a factor of 100, in some examples at least a factor of 1000 larger than a density of the NV centers in the sensing layer 102C outside of the sensing regions 114A.

The sensor chip 704 further comprises a plurality of boundary structures that are configured to confine or guide a motion of the sample objects 112 in the measurement volume 104. In the example of FIG. 7*a*, the boundary structures are sidewalls 104-1, 104-2, 104-3, 104-4 of the measurement volume 104, which form a rectangular enclosure for a carrier fluid and the sample objects 112 contained therein. The distances between opposing sidewalls are chosen such that a uniform close-packing of equal circles or spheres having a diameter d can be placed in the measurement volume 104, wherein the outermost circles or spheres are in contact with the sidewalls 104-1, 104-2, 104-3, 104-4, thus preventing any motion of the circles or spheres parallel to the bottom wall 104-A. The sidewalls 104-1, 104-2, 104-3, 104-4 may for example be arranged similar to the sidewalls of the measurement volume on the sensor chip 200 of FIG. 2. This enables formation of a corresponding self-organized structure of sample objects 112 having a circular cross section with diameter d in the measurement volume 104, e.g. for oblatespheroidic sample objects 112 as illustrated in FIGS. 7*a*, 7*b*.

In the self-organized structure, i.e. in the close-packing of circles, the sample objects 112 form a plurality of subsets, wherein all sample objects 112 within a given subset are arranged as a linear chain along a straight line, e.g. along a horizontal straight line parallel to the X axis as in the example of FIG. 7*a*. Adjacent subsets or linear chains are displaced by a distance $A_1$ along the Y direction with respect to each other, wherein $A_1=\sqrt{3}\, d/2$ in a uniform close-packing of circles. The sidewalls 104-1, 104-2, 104-3, 104-4 may for example be arranged such that the self-organized structure comprises between 5 and 20 linear chains, each of which may e.g. comprise between 10 and 100 sample objects.

In other embodiments, the arrangement of the sidewalls 104-1, 104-2, 104-3, 104-4 may be different and/or the boundary structures of the sensor chip 704 may comprise other elements such as guiding walls and/or hydrophilic and/or hydrophobic coatings in addition to or instead of the sidewalls 104-1, 104-2, 104-3, 104-4, e.g. as described above for the sensor chips 200, 300, and 310. The respective boundary structures of the sensor chip 704 are arranged such that when sample objects 112 having a circular cross section with a diameter d are placed in the measurement volume 104 with the sample objects 112 covering the entire first wall 104-A of the measurement volume 104, the sample objects 112 arrange in a self-organized structure in which a plurality of subsets of the sample objects 112 are arranged along a respective one of a plurality of straight lines, e.g. in a rectangular grid with spacings $a_1$ and $a_2$ as in the examples of FIGS. 3*a* and 3*b*.

The sensing device 700 further comprises an illumination system 706 for illuminating the sensing elements 115A in the sensing layer 102C. The illumination system 706 is configured to split an incoming light beam 708, which may e.g. be generated by an external light source such as a laser (not shown), into a plurality of illumination light beams 710, which may also be referred to as illumination beams in the following. For this, the illumination system 706 comprises a plurality of beam splitter 712 and a micromirror 714 along an optical path of the incoming light beam 708. Each of the beam splitters 712 is configured to split off a portion of the incoming light beam 708 to generate a respective one of the illumination beams 710. The beam splitters 712 may for example be polarizing or non-polarizing beam splitters and preferably are configured such that the incoming light beam 708 is split into equal parts, i.e. such that each of the illumination beams 710 has the same optical power. The micromirror 714 is configured to reflect a remaining portion of the incoming light beam 708 after having passed through the beams splitters 710 to create another illumination beam 710. The beam splitters 712 and the micromirror 714 may for example be arranged on the frame of the mount 702 and may be adjustable, e.g. tiltable around one or two axes, to align the respective illumination beam 710.

The illumination system 706 is configured to provide the plurality of illumination beams 710 such that each of the illumination beams 710 propagates through the substrate 102 of the sensor chip 704 along an optical path that is aligned with a respective one of the subsets of sample objects 112, i.e. aligned with the respective straight line along which the sample objects 112 of the subset are arranged. Thereby, sensing elements 115 adjacent to the sample objects 112 of the respective subsets in the self-organize structure can be illuminated by the illumination beam 710. An illumination beam or an optical path is referred to as aligned with the respective straight line if the respective optical path extends in a plane containing the straight line, i.e. such that the optical path overlaps with the straight line when viewed along a direction in the plane that is perpendicular to the straight line. In some embodiments, the optical path may extend parallel or under a small angle to the straight line, e.g. parallel or under a small angle to the sensing layer 102C and/or the bottom wall 104-A of the measurement volume 104, whereas in other embodiments, the optical path may for example form a zig-zag pattern in the respective plane, e.g. as detailed below with reference to FIG. 7*b*.

In the example of FIG. 7*a*, the illumination beams 710 are parallel to each other and propagate along the X direction. The illumination beams 710 may for example propagate parallel to the bottom wall 104-A of the measurement volume 104 or under a small angle to the bottom wall 104-A, e.g. under an angle smaller than 10°, in some examples smaller than 5°, in one example smaller than 2°, for example as shown in FIG. 9. A spacing $A_1$ between adjacent illumination beams 710 corresponds to the distance between adjacent linear chains of sample objects 112 in the self-organized structure, i.e. $A_1=\sqrt{3}\ d/2$ for a close-packing of equal circles or spheres. Each illumination beam 710 passes underneath the centers of the sample objects 112 of the respective linear chain when viewed perpendicular to the bottom wall 104-A of the measurement volume 104 as in FIG. 7*a*. Each of the illumination beams 710 may thus for example illuminate a strip-like portion 710A of the sensing layer 102C underneath the respective subset of sample objects 112, wherein only a single strip-like portion 710A associated with the uppermost illumination beam 710 is indicated by dash-dotted lines in FIG. 7*a* for simplicity. Adjacent strip-like portions 710A may be separated by portions of the sensing layer 102C that are not illuminated by any of the illumination beams 710, i.e. the illumination beams 710 may create a pattern of spatially separated strips of light.

In some embodiments, the illumination system 706 may comprise one or more diffractive optical elements (not shown) instead of or in addition to the beam splitters 712 and the micromirror 714. Each of the diffractive optical elements may be configured to split an incident beam of light such as the incoming light beam 708 into two or more beams such as the illumination light beams 710 by means of diffraction. Each of the diffractive optical elements may for example be configured to imprint a phase pattern and/or an intensity pattern onto the incident beam, wherein interference between different parts of the incoming beam causes the incident beam to split into the two or more beams. Each of the diffractive optical elements may e.g. comprise a phase mask and/or a diffraction grating. The illumination system 706 may further comprise one or more focusing elements such as one or more lenses, wherein the one or more focusing elements may for example be configured to refract and/or deflect the two or more beams created by the diffractive optical elements, some or all of which may propagate under an angle relative to the incident beam, e.g. to form a pattern of parallel beams similar to the one shown in FIG. 7*a*. For this, a diffractive optical element may for example be arranged in the focal plane of a respective focusing element.

In some embodiments, the illumination system 706 may also comprise one or more light sources such as lasers (not shown), e.g. for generating one or more incoming light beams and/or for generating one or more illumination beams 710. In some examples, the illumination system 706 may comprise a respective light source for each of the illumination beams 710 or for each of a plurality of subsets of the illuminations beams 710.

In the example of FIG. 7*b*, the illumination system 706 further comprises optical coatings 716, 718, which are arranged on the bottom wall 104-A of the measurement volume 104 and on a bottom surface of the substrate 102, respectively. Each of the optical coatings 716, 718 is a reflective coating that is configured to reflect the illumination beams 710. Preferably, the optical coating 716 on the bottom wall 104-A, which is adjacent to the sensing layer 102C, is a broadband reflective coating that is configured to reflect light both at an absorption wavelength of the sensing elements 115A, e.g. at a wavelength of the illumination beams 710, and at an emission wavelength of the sensing elements 115A, which may e.g. correspond to a wavelength of the sensor signals of the sensing elements 115A. The optical coating 718 on the bottom surface of the substrate 102 may be a dichroic reflective coating that is configured to reflect light at the absorption wavelength of the sensing elements 115A and to transmit light at the emission wavelength of the sensing elements 115A, e.g. to reflect the illumination beams 710 while transmitting the sensor signals. The sensor signals may for example be imaged through a backside of the sensor chip 704 onto a photosensitive detector such as the measurement device 408 as illustrated in FIG. 4. In some embodiments, the illumination system 706 may not comprise one or both of the optical coatings 716, 718, but the illumination beams 710 may instead be reflected off the respective surface by total internal reflection.

The illumination system 706 is configured to couple the illumination beams 710 into the sensor chip 704 under an entrance angle α to the bottom wall 104-A and/or the bottom surface of the substrate 102, e.g. through an angled entrance facet 720 on a side face of the substrate 102. In the substrate 102, each of the illumination light beams 710 may be sequentially reflected off the optical coatings 716, 718, thus propagating through the substrate 102 along a zig-zag optical path in a plane parallel to the XZ plane of FIG. 7*b*. The plane in which the zig-zag optical path extends also contains the straight line along which the respective subset of sample objects 112 is arranged. As the optical coatings 716, 718 are arranged on opposite sides of the sensing layer 102C, i.e. above and below the sensing layer 102C, respectively, the optical path of each illumination light beam 710 sequentially intersects with the sensing layer 102C in sensing regions 114A. The sensing regions 114A may for example be the portions of the sensing layer 102C through which the respective illumination light beam 710 passes, i.e. the portions of the sensing layer 102C in which sensing elements 115A are illuminated by the respective illumination beam 710. Sensing elements 115A outside of the sensing regions 114A may not be illuminated by the illumination beams 710. In other words, the illumination beams 710 may create "illumination-induced" sensing regions 114A within a homogeneous sensing layer 102C.

The illumination system 706 is configured to couple the illumination beams 710 into the sensor chip 704 such that each of the sensing regions 114A is adjacent to a respective one of the sample objects 112 in the self-organized structure. In this way, sensing elements 115A in the sensing regions 114A may be addressed selectively with the illumination beams 710, e.g. to activate and/or read out the respective sensing elements 115A, thereby creating an "illumination-induced" array of spatially separated sensors, which is adapted to the self-organized structure of the sample objects 112 in the measurement volume 102. This may for example be achieved by choosing the entrance angle α as well as the entrance point on the entrance facet 720 accordingly, e.g. by adjusting the respective beam splitter 712 or micromirror 714 accordingly. Reflection points of the illuminations beams at the optical coating 716 and thus the sensing regions 114A may for example be separated by a distance $a_2$ equal to the diameter d of the sample objects 112. The refection points and thus the sensing regions 114A may be aligned with a center of a respective one of the sample objects 112 in the self-organized structure as illustrated in FIG. 7*b*.

In other embodiments, the illumination beams 710 may propagate through the sensing layer 102C parallel or under a small angle to the bottom wall 104-A of the measurement volume 104, e.g. under an angle of less than 5°, in one example an angle of less than 2°. Each of the illumination beams 710 may for example be reflected off the bottom wall 104-A, e.g. at the coating 716 or by total internal reflection, a single time, e.g. at a center of the bottom wall 104A along the X direction. Each of the illumination beams 710 may thus for example illuminate a strip-like portion 710A of the sensing layer 102C underneath the respective subset of sample objects 112, e.g. as detailed above with reference to FIG. 7*a*. In such cases, subsets of sensing elements 115A associated with a given sample object 112 may be selected as part of a data processing of the measured sensor signals, e.g. as detailed below for method 800 of FIG. 8. This may for example comprise defining "virtual" sensing regions 114A within the strip-like portions 710A, which may correspond to region-of-interests 710B in a spatially resolved image of the sensing elements 115A in the sensing layer 102C.

In some embodiments, the sensing device 700 may further comprise a measurement device (not shown) for reading out sensor signals from the sensing elements 115A such as the measurement device 408 of the measurement system 400 of FIG. 4. The measurement device may in particular be a photosensitive detector configured to record a spatially resolved image of optical sensor signals of the sensing elements, e.g. a camera chip comprising a plurality of photosensitive pixels such as a CCD or CMOS chip. The sensing device 700 may further comprise a controller (not shown) for selecting regions-of-interests 710B in the spatially resolved image, e.g. as detailed below for method 800 of FIG. 8. The controller may be configured to execute some or all of the steps of a method for parallelized probing of a plurality of samples according to any one of the embodiments described herein, e.g. the method 500 and/or the method 800. In some embodiments, the sensing device 700 or parts thereof, in particular the mount 702 and/or the illumination system 706, may be provided as an integrated system together with a measurement system according to the invention such as the measurement system 400.

FIG. 8 shows a flow diagram of a method 800 for parallelized probing of a plurality of samples in accordance with an exemplary embodiment of the invention. The method 800 may for example be implemented with one of the sensor chips 100, 200, 300, 310, 404, 704, with the measurement system 400, and/or with the sensing device 700. In the following, the method 800 will be described using the sensing device 700 and the system 400 as a non-limiting example for illustration purposes. The method 800 is not limited to the order of execution indicated by the flow diagram of FIG. 8. As far as technically feasible, the method 800 may be executed in an arbitrary order and steps thereof may be executed simultaneously at least in part, e.g. some or all of steps 804 to 81*o* described below.

The method 800 comprises, in step 802, providing a sensor chip with a sensing layer arranged in or on a substrate and a measurement volume adjacent to the sensing layer, wherein the sensing layer comprises a plurality of sensing elements, e.g. similar to step 502 of method 500. For example, a sensor chip such as the sensor chip 704 of the sensing device 700 may be provided, which comprises a plurality of optically addressable sensing elements 115A, in particular nitrogen-vacancy centers, in the sensing layer 102C underneath the measurement volume 104. The sensor chip 704 may for example be mounted in the mount 702 of the sensing device 700 or in the mount 402 of the measurement system 400. This may comprise aligning optical paths of the illumination beams 710 provided by the illumination system 706 relative to the sensor chip 704 or vice-versa, e.g. by adjusting the beam splitters 712 and the micromirror 714.

In step 804, a carrier fluid comprising a plurality of sample objects 112 is provided to the measurement volume 104 of the sensor chip 704, e.g. as described above for step 504 of method 500. In step 806, a number of the sample objects 112 in the measurement volume 104 is controlled such that the sample objects 112 form a self-organized structure, e.g. as described above for step 506 of method 500. The self-organized structure may for example be a close-packing of equal circles or spheres as illustrated in FIG. 7*a*, wherein each of the sample objects 112 is arranged at a pre-determined position within the measurement volume 104.

The method 800 further comprises, in step 808, selecting a respective subset of sensing elements 115A on the sensor chip 704 for each sample 112A on which a measurement is to be performed in step 810, e.g. for each of the samples 112A. A measurement on a sample 112A in step 810 may then be performed using only sensing elements 115A of the respective subset, e.g. by selectively determining sensor signals from these sensing elements 115A. The subsets of sensing elements 115A may be selected prior to formation of the self-organized structure of the sample objects 112 in step 808, e.g. because the positions of the sample objects 112 in the self-organized structure are known a priori, or may be selected after forming the self-organized structure, e.g. based on positions of the sample objects 112 in the self-organized structure that have been determined experimentally, for example using a camera. In some embodiments, the subsets of sensing elements 115A may also be selected after performing the measurements in step 810, e.g. as a part of a data processing of the measured sensor signals.

For selecting the subsets of sensing elements 115A, a region-of-interest 710B may for example be selected for each of the sample objects 112 in the self-organized structure to perform a selective read out of sensing elements associated with the region-of-interest. The region-of-interest 710B may for example be defined as a portion of a spatially resolved image of the sensor chip 704, which may in particular be a microscopic image of the sensing layer 102C recording an intensity of light emitted by the sensing elements 115A as a function of position in the sensing layer 102C in the XY plane of FIG. 7*a*. The region-of-interest 710B in the spatially resolved image may for example correspond to a sensing region 114A in the sensing layer 102C that is adjacent to the respective sample object 112 in the self-organized structure or to a part of this sensing region 114A. The sensing regions 114A may e.g. be spatially separated sensing regions or sensors defined by a non-uniform distribution of the sensing elements 115A in the sensing layer 102C as in the example of FIG. 1*a*, illumination-induced sensing regions defined by intersections of illumination beams with the sensing layer 102C as in the example of FIG. 7*b*, or “virtual” sensing regions, which may e.g. be selected from an illuminated strip-like portion 710A of the sensing layer 102C as in the example of FIG. 7*a* or from a homogeneously illuminated sensing layer 102.

In addition to or instead of selecting regions-of-interest 710B, the subsets of sensing elements 115A may also be selected by selective illumination of the sensing layer 102C, e.g. to selectively activate and/or read out the sensing elements 115A by patterned illumination. This may in particular comprise selectively illuminating the sensing layer 102C with illumination beams 710 as detailed above with reference to FIGS. 7*a*, 7*b*. For example, only sensing elements 115A in the strip-like portions 710A of FIG. 7*a* or only sensing elements 115A in the sensing regions 114A of FIG. 7*a* or 7*b* may be illuminated by the illumination beams 710 and may thus generate sensor signals for probing the samples 112A.

In step 810, a measurement is performed on one or more of the samples 112A while the sample objects 112 are arranged in the self-organized structure in the measurement volume 104, wherein the measurement is performed using the subsets of sensing elements 115A selected in step 808. The measurement may for example be performed by illuminating the sensing elements 115A in the sensing layer 102C with the illumination beams 710 and recording an intensity of light emitted by the sensing elements 115A as the sensor signals using a photosensitive detector such as the measurement device 408. The sensor signals are determined selectively using only sensing elements 115A in the selected subsets, for example by selectively illuminating the sensing elements 115A with the illumination beams 710 and furthermore discarding sensor signals outside of the regions-of-interest 710B, i.e. sensor signals originating from sensing elements 15A outside of the sensing regions 114A.

Thereby, the method 800 allows for the parallelized probing of a plurality of samples with a sensor chip that is re-usable, can be manufactured easily and is simple to handle. Only a small number of boundary structures is used for arranging the sample objects in a well-defined and reproducible self-organized structure such that no microscopic structures like microfluidic sample wells are required, which complicate the manufacturing process as well as sample preparation on the sensor chip and are almost impossible to clean. Moreover, a selective probing of the respective samples may be performed even using a homogeneous sensing layer with a uniform distribution of sensing elements, which further simplifies manufacturing of the sensor chip.

FIG. 9 depicts a schematic illustration (not to scale) of a sensor chip 900 of the sensing device 700 according to another exemplary embodiment of the invention in side view. The sensor chip 900 is similar to the sensor chip 704 of FIG. 7*b*, wherein corresponding elements are labelled using the same reference signs as in FIG. 7 and description thereof is omitted for the sake of brevity.

In the example of FIG. 9, the illumination beams 710 are coupled into the sensor chip 900 through a side face of the substrate 102, e.g. using the illumination system 706 of the sensing device 700, such that the illumination beams 710 propagate through the sensing layer 102C under an angle β to the bottom wall 104-A of measurement volume 104. The angle β may for example be chosen such that the optical paths of the illumination beams 710 remain within the sensing layer 102C throughout the substrate 102 and/or such that the illumination beams 710 can be reflected off the bottom wall 104-A by total internal reflection. Preferably, each illumination beam 710 is reflected off the bottom wall 104-A a single time, e.g. at the center of the measurement volume 104 along the X axis as shown in FIG. 9, for example by total internal reflection. The angle β may for example be between 0° and 5°, in one example between 0.5° and 2°. Each of the illumination beams 710 may thus for example illuminate a strip-like portion of the sensing layer 102C underneath a respective subset of sample objects 112, e.g. as shown in FIG. 7*a*.

Within the sensing layer 102C, sensing regions 114A associated with respective sample objects 112 in a self-organized structure in the measurement volume 104 may for example be selected or defined by selective determination of sensor signals from sensing elements 115A in the corresponding regions, e.g. by only detecting light emitted by NV centers in certain portions of the sensing layer 102C.

In some embodiments, the sensor chip 900 may comprise a plurality of microlenses 902, in particular solid immersion lenses as in the example of FIG. 9, which may e.g. be arranged on or adjacent to a bottom surface of the substrate 102 as shown in FIG. 9. In other examples, the microlenses 902 may for example be provided as part of the sensing device 700 or the measurement system 400. Each microlens 902 may define a corresponding sensing region 114A in the sensing layer 102C, wherein the sensing region 114A may for example comprise all sensing elements 115A within a field-of-view of the respective microlens 902. Each microlens 902 may be configured to collect light emitted by the sensing elements 115A in the corresponding sensing region 114A, thereby allowing for selectively determining sensor signals from the sensing elements 115A in the corresponding sensing region 114A. The microlenses 902 may be arranged in a one-dimensional or preferably two-dimensional array, which defines a corresponding array of sensing regions 114A in the sensing layer 102C, e.g. as illustrated in FIG. 7*a*.

Additionally or alternatively, the sensing regions 114A may for example be defined by a pinhole array 904, which may e.g. be provided as part of the sensing device 700 or of the measurement system 400. The pinhole array 904 comprises a plurality of pinholes or open-ings, each of which is associated with a respective sensing region 114A in the sensing layer 102C. Each pinhole is configured to transmit light originating from the respective sensing region 114A while light originating from outside the respective sensing region 114A, in particular adjacent portions of the sensing layer 102C, is blocked by the pinhole array 904. This also allows for selectively determining sensor signals from the sensing elements 115A in the corresponding sensing region 114A. The pinhole array 904 may for example be arranged in an image plane of the microlenses 902 as shown in FIG. 9 or in an image plane of an imaging system (not shown) of the measurement system 400. In other embodiments, the pinhole array 904 may e.g. be arranged on or adjacent to the bottom surface of the substrate 102 or on or adjacent to the measurement device 408 of the measurement system 400, which may e.g. be a camera comprising a CCD or CMOS chip. The pinholes of the pinhole array 904 may be arranged in a one-dimensional or preferably two-dimensional array, which defines a corresponding array of sensing regions 114A in the sensing layer 102C, e.g. as illustrated in FIG. 7*a*.

In some embodiments, the sensing regions 114A may also be defined by the measurement device 408 of the measurement system 400, e.g. in addition to or instead of the microlenses 902 and/or the pinhole array 904. The measurement device 408 may for example comprise a plurality of spatially separated measuring elements 410, each of which is associated with a respective one of the sensing regions 114A as illustrated in FIG. 9. The measuring elements 410 may e.g. be photosensitive elements such as photodiodes, CCD or CMOS chips or spatially separated pixels of a CCD or CMOS chip. The microlenses 902 or the imaging system (not shown) of the measurement system 400 may for example be configured to image light originating from a sensing region 114A onto the respective photosensitive element 410, which may be configured to determine an intensity of the light. Accordingly, a sensing region 114A may be defined as the region within the sensing layer 102C that is imaged onto the respective photosensitive element 410. A spacing $a_2$ between adjacent sensing regions 114A may correspond to a spacing between adjacent photosensitive elements 410 divided by a magnification of the imaging and a size of the sensing regions 114A may correspond to a size of the photosensitive elements 410 divided by the magnification of the imaging. In other examples, the photosensitive elements 410 may be arranged in close proximity to the sensor chip 900, e.g. on or adjacent to the bottom surface of the substrate, which may allow for collecting light from the respective sensing region 114A without requiring an imaging system. The photosensitive elements 410 may be arranged in a one-dimensional or preferably two-dimensional array, which defines a corresponding array of sensing regions 114A in the sensing layer 102C, e.g. as illustrated in FIG. 7*a*. By using a measurement device 408 with spatially separated photosensitive elements 410 associated with respective sensing regions 114A, the number of photosensitive elements 410 may be reduced, e.g. compared to a continuous camera chip with a plurality of pixels covering the same area. This may reduce the amount of data that has to be processed and may speed up read-out of the measurement device 408.

The sensor chip 900, the pinhole array 904, and/or the measurement device 408 may be used with the sensing device 700 of FIG. 7*a*, e.g. to select sensing regions 114A from the strip-like portions 710A illuminated by the illumination beams 710. In other examples, a different sensor chip and/or a different type of illumination may be used and the sensing regions 114A may defined in a similar way, e.g. in a homogeneously illuminated sensing layer, in a selectively illuminated sensing layer as in FIG. 7*b*, and/or in a sensing layer comprising spatially separated sensing regions as in FIG. 1*b*. In other words, individually addressable and distinguishable sensing regions may be obtained by one or more of a spatially inhomogeneous or selective distribution of sensing elements in the sensing layer, a spatially inhomogeneous or selective illumination of the sensing layer, and a spatially inhomogeneous or selective detection of sensor signals from the sensing layer. Thereby, the sample objects 112 in the self-organized structure can be probed individually using the sensing elements of the respective sensing region.

The embodiments of the present invention disclosed herein only constitute specific examples for illustration purposes. The present invention can be implemented in various ways and with many modifications without altering the underlying basic properties. Therefore, the present invention is only defined by the claims as stated below.

LIST OF REFERENCE SIGNS

100—sensor chip
102—substrate
102A—lower substrate
102B—upper substrate/cover
104—measurement volume
104-A—bottom wall
104-B—top wall
104-1, 104-2, 104-3, 104-4—sidewalls
104*a*—proximal portion
104*b*—center portion
104*c*—distal portion
106, 106A, 106B—input ports
108, 108A, 108B—output ports
110—droplet generator
112—sample object
112A—sample
112B—shell layer
114A, 114B—sensor/sensing region
115A, 115B—sensing elements
116—unit cell
200—sensor chip
202—inlet channel
204—outlet channel
206—valve
300—sensor chip
302—guiding wall
310—sensor chip
312—coating
400—measurement system
402—mount
404—sensor chip
406—microfluidics unit
408—measurement device
410—measuring element
412—controller
414—light source
416—camera
418—sorting unit
500—method for parallelized probing of a plurality of samples

502—step of providing a sensor chip
504—step of providing a carrier fluid comprising a plurality of sample objects
506—step of forming a self-organized structure of sample objects
508—step of performing a measurement on one or more samples
700—sensing device
702—mount
704—sensor chip
706—illumination system
708—incoming light beam
710—illumination light beams
710A—strip-like portion
710B—region-of-interest
712—beam splitters
714—micromirror
716—broadband reflective coating
718—dichroic reflective coating
720—entrance facet
800—method for parallelized probing of a plurality of samples
802—step of providing a sensor chip
804—step of providing a carrier fluid comprising a plurality of sample objects
806—step of forming a self-organized structure of sample objects
808—step of selecting subsets of sensing elements in sensing regions
810—step of performing a measurement on one or more samples using the selected subsets
900—sensor chip
902—microlens
904—pinhole array
$a_1$, $a_2$—spacing of sensor array
D, $D_1$, $D_2$—distance between sidewalls
d—diameter of sample objects
$A_1$—distance between optical paths of illumination light beams
α—entrance angle of illumination light beams

The invention claimed is:

1. A method for parallelized probing of a plurality of samples, the method comprising:

providing a sensor chip, the sensor chip comprising a sensing layer arranged in or on a substrate and a measurement volume adjacent to the sensing layer, wherein the sensing layer comprises a plurality of sensing elements, each of which is configured to generate a sensor signal characterizing a physical observable in the vicinity of the respective sensing element;

providing a carrier fluid comprising a plurality of sample objects to the measurement volume, wherein each of the sample objects comprises or forms a respective sample;

controlling a number of sample objects in the measurement volume such that the sample objects form a self—organized structure in the measurement volume, wherein the self—organized structure is a structure in which the arrangement of the sample objects is at least in part defined by interactions between the sample objects themselves; and performing a measurement on one or more of the samples while the sample objects are arranged in the self—organized structure, wherein a measurement on a sample is performed using one or more sensing elements arranged adjacent to the respective sample object in the self—organized structure.

2. The method of claim 1, wherein performing the measurement on the one or more samples comprises, for each of the one or more samples, selecting a subset of the sensing elements, the sensing elements in the subset being arranged in a sensing region adjacent to the respective sample object in the self—organized structure, and selectively determining sensor signals from the sensing elements in the sensing region.

3. The method of claim 1, wherein:

the sensing elements in the sensing layer form an array of spatially separated sensors, each of the sensors comprising one or more sensing elements;

a respective sample object is arranged adjacent to each of the sensors in the self—organized structure; and a measurement on a sample is performed using the respective sensor.

4. The method of claim 1, wherein the sample objects are microdroplets dispersed in the carrier fluid.

5. The method of claim 1, wherein:

the sensor chip comprises boundary or guiding structures configured to confine or guide a motion of the sample objects within the measurement volume; and the self—organized structure is formed by interactions between the sample objects and the boundary or guiding structures as well as by surface—surface interactions between the sample objects.

6. The method of claim 1, wherein the sample objects have a circular cross section and the self—organized structure is a close—packing of equal circles.

7. The method of claim 1, wherein the carrier fluid comprising the sample objects is provided through a microfluidic inlet channel that is in fluid communication with the measurement volume and controlling the number of sample objects in the measurement volume comprises maintaining a flow of the carrier fluid comprising the sample objects through the inlet channel until the self—organized structure is formed.

8. The method of claim 1, wherein the sensing elements are optically addressable solid—state spin systems and performing a measurement on a sample comprises:

illuminating solid—state spin systems arranged in a sensing region adjacent to the respective sample object in the self—organized structure with light to optically excite the solid—state spin systems in the sensing region; and detecting an optical signal emitted by the solid—state spin systems in the sensing region.

9. A sensor chip for parallelized probing of a plurality of samples, the sensor chip comprising:

a measurement volume configured to receive a carrier fluid comprising a plurality of sample objects, each of the sample objects comprising or forming a respective sample;

an array of sensors arranged in or adjacent to a first wall of the measurement volume, wherein the sensor array has a first spacing $a_1$ and each of the sensors comprises one or more sensing elements, each of which is configured to generate a sensor signal characterizing a physical observable in the vicinity of the respective sensing element; and two or more boundary or guiding structures configured to confine or guide a motion of the sample objects in the measurement volume, wherein the two or more boundary or guiding structures are arranged such that when a close—packing of solid objects having a circular cross section with a diameter d equal to the first spacing $a_1$ is placed in the measurement volume with the close—packing of the solid objects covering the entire first wall of the measurement volume, the two or more boundary or guiding structures confine the solid objects such that a respective solid object is centrally aligned with each of the sensors.

10. The sensor chip of claim 9, wherein the boundary or guiding structures comprise one or more of:

a sidewall of the measurement volume, wherein the sidewall extends under an angle to the first wall;

a guiding wall protruding from one or both of the first wall of the measurement volume and a second wall of the measurement volume opposing the first wall;

a hydrophilic coating on one or both of the first and second walls of the measurement volume; and a hydrophobic coating on one or both of the first and second walls of the measurement volume.

11. The sensor chip of claim 9, wherein each of the outermost sensors in the sensor array is arranged at a distance corresponding to one half of the first spacing $a_1$ from at least one of the boundary or guiding structures.

12. The sensor chip of claim 9, wherein the two or more boundary or guiding structures comprise two opposing boundary or guiding structures that are separated by a distance D with $$D = M \cdot a_1 \text{ or } D = \left(1 + \sqrt{3}N/2\right) \cdot a_1,$$

wherein M and N are positive integers.

13. The sensor chip of claim 9, wherein the sensor array is a two—dimensional periodic array having the first spacing $a_1$ in a first direction and a second spacing $a_2$ in a second direction.

14. The sensor chip of claim 9, wherein the sensor chip comprises a microfluidic inlet channel and a microfluidic outlet channel, the inlet and outlet channels being in fluid communication with the measurement volume, wherein the sensor chip further comprises means for selectively preventing the sample objects from leaving the measurement volume through the outlet channel.

15. The sensor chip of claim 9, wherein the sensing elements are optically addressable solid—state spin systems.

16. A sensing device for parallelized probing of a plurality of samples, the sensing device comprising:

a sensor chip comprising a substrate and a measurement volume configured to receive a carrier fluid comprising a plurality of sample objects, each of the sample objects comprising or forming a respective sample, wherein the substrate comprises a plurality of optically addressable sensing elements arranged in a sensing layer in or below a first wall of the measurement volume, each of the sensing elements being configured to generate a sensor signal characterizing a physical observable in the vicinity of the respective sensing element; and an illumination system for illuminating the sensing elements, wherein:

the sensor chip further comprises two or more boundary or guiding structures configured to confine or guide a motion of the sample objects in the measurement volume, the two or more boundary or guiding structures being arranged such that when solid objects having a circular cross section with a diameter d are placed in the measurement volume with the solid objects covering the entire first wall of the measurement volume, the solid objects arrange in a self—organized structure in which a plurality of subsets of the solid objects are each arranged along a respective one of a plurality of straight lines; and the illumination system is configured to provide a plurality of illumination light beams, each of which propagates through the substrate along an optical path aligned with a respective one of the plurality of straight lines for illuminating sensing elements adjacent to the solid objects of the respective subset in the self—organized structure.

17. The sensing device of claim 16, wherein the optical paths of the illumination light beams are parallel to each other and separated by a spacing $A_1$ with $$A_1 = d \text{ or } A_1 = \sqrt{3}\, d/2.$$

18. The sensing device of claim 16, wherein one or both of:

one or more of the optical paths of the illumination light beams extend through the sensing layer at an angle of less than 10° to the first wall of the measurement volume; and for one or more of the optical paths of the illumination light beams, light propagating along the respective optical path is sequentially reflected off a first surface above the sensing layer and a second surface below the sensing layer such that the optical path intersects with the sensing layer in sensing regions with each of the sensing regions being adjacent to a respective one of the solid objects in the self—organized structure.

19. The sensing device of claim 16, wherein each of the sensing elements is configured to generate an optical sensor signal and the sensing device further comprises:

a photosensitive detector configured to record a spatially resolved image of the sensor signals of the sensing elements; and a controller configured to select, for each of at least some of the solid objects in the self—organized structure, a region—of—interest in the spatially resolved image, wherein the region—of—interest contains sensor signals originating from a sensing region adjacent to the respective solid object in the self—organized structure.

20. The sensing device of claim 16, wherein the sensing elements are optically addressable solid—state spin systems.

* * * * *